US011535641B2

(12) United States Patent
Groeneveld et al.

(10) Patent No.: US 11,535,641 B2
(45) Date of Patent: Dec. 27, 2022

(54) METHOD FOR PREPARING GOS HAVING REDUCED ALLERGENICITY

(71) Applicant: FRIESLANDCAMPINA NEDERLAND B.V., Amersfoort (NL)

(72) Inventors: Dirk Andries Groeneveld, Wageningen (NL); Bas Johan Henri Kuipers, Wageningen (NL); Bernardina Johanna Martina Delsing, Wageningen (NL); Linqiu Cao, Wageningen (NL)

(73) Assignee: FrieslandCampina Nederland B.V., Amersfoort (NL)

( * ) Notice: Subject to any disclaimer, the term of this patent is extended or adjusted under 35 U.S.C. 154(b) by 282 days.

(21) Appl. No.: 16/729,172

(22) Filed: Dec. 27, 2019

(65) Prior Publication Data

US 2020/0115407 A1    Apr. 16, 2020

Related U.S. Application Data

(63) Continuation of application No. PCT/EP2018/067134, filed on Jun. 26, 2018.

(30) Foreign Application Priority Data

Jun. 28, 2017    (EP) .................................. 17178462

(51) Int. Cl.
*A61K 31/702*    (2006.01)
*C12P 19/14*    (2006.01)
*C12N 9/38*    (2006.01)
*C07H 3/06*    (2006.01)

(52) U.S. Cl.
CPC ............. *C07H 3/06* (2013.01); *A61K 31/702* (2013.01); *C12N 9/2471* (2013.01); *C12P 19/14* (2013.01); *C12Y 302/01023* (2013.01)

(58) Field of Classification Search
None
See application file for complete search history.

(56) References Cited

U.S. PATENT DOCUMENTS

2019/0119662 A1*    4/2019    Hoshi .................. C12N 9/2471

FOREIGN PATENT DOCUMENTS

WO    WO-2017/115826    7/2017

OTHER PUBLICATIONS

Soh et al., "Anaphylaxis to galacto-oligosaccharides—an evaluation in an atopic population in Singapore", Allergy 70:1020-1023, 2015 (Year: 2015).*
International Search Report and Written Opinion issued in International Application No. PCT/EP2018/067134, dated Jul. 27, 2018.
Anonymous: "Galactooligosaccharide"; Wikipedia, Jan. 1, 2017;(XP055399393); Retrieved from the Internet: https://en.wikipedia.org/wiki/Galactooligosaccharide; [retrieved on Aug. 17, 2017].
Kaneko, et al.; "Development of hypoallergenic galactooligosaccharides on the basis of allergen analysis"; Bioscience Biotechnology Biochgemistry, vol. 78, No. 1; Jan. 2, 2014; pp. 100-108; (XP055416611).
Ohtsuka, et al.; "Purification and Properties of a β-Galactosidase with High Galactosyl Transfer Activity from Cryptococcus laurentii OKN-4", Journal of Fermentation and Bioengineering, Society of Fermentation Technology, JP, vol. 70, No. 5; Jan. 1, 1990; pp. 301-307; (XP025777417).
Soh, et al.; "An unusual cause of food-induced anaphylaxis in mothers", World Allergy Organization Journal, Biomed Central Ltd, London, UK, vol. 10, No. 1; Feb. 10, 2017; pp. 1-5; (XP021241717).
Guerrero et al., "Transgalactosylation and hydrolytic activities of commercial preparations of Beta-galactosidase for the synthesis of prebiotic carbohydrates", Enzyme and Microbial Technology, 2014, vol. 70, pp. 9-17 (9 pages).

* cited by examiner

*Primary Examiner* — David Steadman
(74) *Attorney, Agent, or Firm* — Sunit Talapatra; Foley & Lardner, LLP

(57) ABSTRACT

The invention relates to the field of nutritional ingredients, in particular to methods for producing hypoallergenic galacto-oligosaccharides (GOS) and the use thereof in food and drink items. Provided is the use of a beta-galactosidase (EC 3.2.1.23) derived from *Cryptococcus terrestris* (recently renamed *Papiliotrema terrestris*) in the production of a hypoallergenic GOS preparation having a reduced capacity to induce an allergic response in a subject.

6 Claims, 14 Drawing Sheets

Specification includes a Sequence Listing.

Figure 1a

Met Ile Pro Ala Ser Ala Leu Leu Ala Ala Val Pro Leu Leu Ala Gln

Gln Val Ser Ala Gly Ile Leu Arg Arg Gln Asn Ala Ala Gly Ser Asp

Ser Ala Ala Pro Asp Ser Ile Ala Asp Ala Ser Thr Gly Val Val Ser

Ser Ile Ala Thr Glu Ala Val Ser Ser Gly Ala Thr Gly Leu Val Ala

Ser Val Ala Met Ser Phe Ala Ser Ser Met Ala Thr Pro Thr Ala Thr

Val Thr Gly Leu Ser Ser Glu Thr Gly Ala Pro Ser Asn Thr Pro Met

Ala Ser Ala Ser Gly Ser Val Pro Thr Thr Thr Ser Ala Val Gly Ser

Gly Asp Phe Asp Trp Val Gln Thr Asp Gly Leu Pro Thr Ile Thr Thr

Thr Leu Ala Thr Thr Asn Gln Asp Ala Ile Thr Pro Thr Ala Thr Gly

Pro Val Gly Gly Gln Gly Thr Pro Ala Val Asn Phe Thr Asp Tyr Ser

Ser Ser Ser Leu Glu Gln Phe Trp Asn Asp Trp Val Gly Glu Val Glu

Glu Pro Pro Phe Ala Tyr Val Pro Glu Pro Pro Asn Pro Tyr Pro Leu

Pro Asn Ala Pro Pro Pro Ile Tyr Pro Glu Tyr Tyr Thr Lys Arg Pro

Lys Asp Ile Leu Pro Asp Tyr Lys Phe Pro Lys Asp Phe Leu Phe Gly

Trp Ala Thr Ala Ala Gln Gln Trp Glu Gly Ala Val Lys Ala Asp Gly

Lys Gly Pro Ser Ile Trp Asp Trp Ala Ser Arg Phe Pro Gly Phe Ile

Ala Asp Asn Thr Thr Ser Asp Val Gly Asp Leu Gly Tyr Tyr Leu Tyr

Lys Glu Asp Leu Ala Arg Ile Ala Ala Leu Gly Ala Asn Val Tyr Ser

Figure 1b

Phe Ser Met Phe Trp Thr Arg Ile Phe Pro Phe Gly Lys Ala Asp Ser
Pro Val Asn Gln Ala Gly Ile Asp Phe Tyr His Asp Leu Ile Asp Tyr
Ser Trp Ser Leu Gly Ile Glu Pro Val Val Thr Leu Phe His Trp Asp
Thr Pro Leu Ala Leu Gln Leu Glu Tyr Gly Gly Phe Ala Ser Glu Arg
Ile Ile Asp Asp Tyr Val Asn Tyr Ala Glu Thr Val Phe Lys Ala Tyr
Asn Gly Ser Val His Lys Trp Val Thr Phe Asn Glu Pro Val Val Phe
Cys Ser Gln Met Ala Ala Pro Val Asn Thr Thr Leu Pro Pro Asn Leu
Asn Ser Thr Ile Tyr Pro Tyr Thr Cys Ser Tyr His Leu Val Leu Ala
His Ala Lys Thr Val Lys Arg Phe Arg Glu Leu Asn Ile Gln Gly Gln
Ile Ala Phe Lys Ser Asp Asn Phe Val Gly Ile Pro Trp Arg Glu Gly
Asn Gln Glu Asp Ile Asp Ala Val Glu Arg His Gln Ala Tyr Gln Ile
Gly Ile Phe Ala Glu Pro Ile Tyr Asn Thr Gly Asp Trp Pro Asp Ile
Val Lys Asn Asp Leu Ser Pro Asp Ile Leu Pro Arg Phe Thr Asp Asp
Glu Ile Ala Met Ile Lys Cys Thr Ala Asp Phe Phe Pro Ile Asp Gly
Tyr Arg Asp Gly Tyr Val Gln Ala Val Pro Gly Gly Val Glu Ala Cys
Val Ala Asn Ile Ser Asn Pro Leu Trp Pro Ala Cys Asn Gln Val Asn
Phe Tyr Asp Ser Thr Pro Ala Gly Trp Ala Ile Gly Thr Phe Gly Asn
Trp Pro Thr Thr Pro Trp Leu Gln Asn Thr Trp Gln Phe Val Arg Pro

Figure 1c

Phe Leu Ala Asp Leu Ala Lys Arg Tyr Pro Thr Glu Gly Gly Ile Tyr

Leu Ser Glu Phe Gly Phe Ser Glu Pro Phe Glu Asn Asp Lys Thr Phe

Ile Tyr Gln Ile Thr Gln Asp Ser Gly Arg Thr Ala Tyr Phe Asn Ser

Tyr Leu Gly Glu Val Leu Lys Gly Ile Val Glu Asp Gly Ile Pro Ile

Lys Gly Val Phe Gly Trp Ser Met Val Asp Asn Phe Glu Trp Asn Ser

Gly Leu Ser Thr Arg Phe Gly Val Gln Tyr Val Asp Tyr Asn Ser Pro

Thr Arg Gln Arg Thr Phe Lys Arg Ser Ala Leu Glu Met Ser Glu Phe

Trp Asn Ala His Arg Cys Ser Ala

Figure 1d

Ala Thr Thr Asn Gln Asp Ala Ile Thr Pro Thr Ala Thr Gly Pro Val

Gly Gly Gln Gly Thr Pro Ala Val Asn Phe Thr Asp Tyr Ser Ser Ser

Ser Leu Glu Gln Phe Trp Asn Asp Trp Val Gly Glu Val Glu Glu Pro

Pro Phe Ala Tyr Val Pro Glu Pro Pro Asn Pro Tyr Pro Leu Pro Asn

Ala Pro Pro Pro Ile Tyr Pro Glu Tyr Tyr Thr Lys Arg Pro Lys Asp

Ile Leu Pro Asp Tyr Lys Phe Pro Lys Asp Phe Leu Phe Gly Trp Ala

Thr Ala Ala Gln Gln Trp Glu Gly Ala Val Lys Ala Asp Gly Lys Gly

Pro Ser Ile Trp Asp Trp Ala Ser Arg Phe Pro Gly Phe Ile Ala Asp

Asn Thr Thr Ser Asp Val Gly Asp Leu Gly Tyr Tyr Leu Tyr Lys Glu

Asp Leu Ala Arg Ile Ala Ala Leu Gly Ala Asn Val Tyr Ser Phe Ser

Met Phe Trp Thr Arg Ile Phe Pro Phe Gly Lys Ala Asp Ser Pro Val

Asn Gln Ala Gly Ile Asp Phe Tyr His Asp Leu Ile Asp Tyr Ser Trp

Ser Leu Gly Ile Glu Pro Val Val Thr Leu Phe His Trp Asp Thr Pro

Leu Ala Leu Gln Leu Glu Tyr Gly Gly Phe Ala Ser Glu Arg Ile Ile

Asp Asp Tyr Val Asn Tyr Ala Glu Thr Val Phe Lys Ala Tyr Asn Gly

Ser Val His Lys Trp Val Thr Phe Asn Glu Pro Val Val Phe Cys Ser

Gln Met Ala Ala Pro Val Asn Thr Thr Leu Pro Pro Asn Leu Asn Ser

Thr Ile Tyr Pro Tyr Thr Cys Ser Tyr His Leu Val Leu Ala His Ala

Figure 1e

Lys Thr Val Lys Arg Phe Arg Glu Leu Asn Ile Gln Gly Gln Ile Ala
Phe Lys Ser Asp Asn Phe Val Gly Ile Pro Trp Arg Glu Gly Asn Gln
Glu Asp Ile Asp Ala Val Glu Arg His Gln Ala Tyr Gln Ile Gly Ile
Phe Ala Glu Pro Ile Tyr Asn Thr Gly Asp Trp Pro Asp Ile Val Lys
Asn Asp Leu Ser Pro Asp Ile Leu Pro Arg Phe Thr Asp Asp Glu Ile
Ala Met Ile Lys Cys Thr Ala Asp Phe Phe Pro Ile Asp Gly Tyr Arg
Asp Gly Tyr Val Gln Ala Val Pro Gly Gly Val Glu Ala Cys Val Ala
Asn Ile Ser Asn Pro Leu Trp Pro Ala Cys Asn Gln Val Asn Phe Tyr
Asp Ser Thr Pro Ala Gly Trp Ala Ile Gly Thr Phe Gly Asn Trp Pro
Thr Thr Pro Trp Leu Gln Asn Thr Trp Gln Phe Val Arg Pro Phe Leu
Ala Asp Leu Ala Lys Arg Tyr Pro Thr Glu Gly Gly Ile Tyr Leu Ser
Glu Phe Gly Phe Ser Glu Pro Phe Glu Asn Asp Lys Thr Phe Ile Tyr
Gln Ile Thr Gln Asp Ser Gly Arg Thr Ala Tyr Phe Asn Ser Tyr Leu
Gly Glu Val Leu Lys Gly Ile Val Glu Asp Gly Ile Pro Ile Lys Gly
Val Phe Gly Trp Ser Met Val Asp Asn Phe Glu Trp Asn Ser Gly Leu
Ser Thr Arg Phe Gly Val Gln Tyr Val Asp Tyr Asn Ser Pro Thr Arg
Gln Arg Thr Phe Lys Arg Ser Ala Leu Glu Met Ser Glu Phe Trp Asn
Ala His Arg Cys Ser Ala

Figure 1f

Ala Ile Thr Pro Thr Ala Thr Gly Pro Val Gly Gly Gln Gly Thr Pro

Ala Val Asn Phe Thr Asp Tyr Ser Ser Ser Ser Leu Glu Gln Phe Trp

Asn Asp Trp Val Gly Glu Val Glu Glu Pro Pro Phe Ala Tyr Val Pro

Glu Pro Pro Asn Pro Tyr Pro Leu Pro Asn Ala Pro Pro Pro Ile Tyr

Pro Glu Tyr Tyr Thr Lys Arg Pro Lys Asp Ile Leu Pro Asp Tyr Lys

Phe Pro Lys Asp Phe Leu Phe Gly Trp Ala Thr Ala Ala Gln Gln Trp

Glu Gly Ala Val Lys Ala Asp Gly Lys Gly Pro Ser Ile Trp Asp Trp

Ala Ser Arg Phe Pro Gly Phe Ile Ala Asp Asn Thr Thr Ser Asp Val

Gly Asp Leu Gly Tyr Tyr Leu Tyr Lys Glu Asp Leu Ala Arg Ile Ala

Ala Leu Gly Ala Asn Val Tyr Ser Phe Ser Met Phe Trp Thr Arg Ile

Phe Pro Phe Gly Lys Ala Asp Ser Pro Val Asn Gln Ala Gly Ile Asp

Phe Tyr His Asp Leu Ile Asp Tyr Ser Trp Ser Leu Gly Ile Glu Pro

Val Val Thr Leu Phe His Trp Asp Thr Pro Leu Ala Leu Gln Leu Glu

Tyr Gly Gly Phe Ala Ser Glu Arg Ile Ile Asp Asp Tyr Val Asn Tyr

Ala Glu Thr Val Phe Lys Ala Tyr Asn Gly Ser Val His Lys Trp Val

Thr Phe Asn Glu Pro Val Val Phe Cys Ser Gln Met Ala Ala Pro Val

Asn Thr Thr Leu Pro Pro Asn Leu Asn Ser Thr Ile Tyr Pro Tyr Thr

Cys Ser Tyr His Leu Val Leu Ala His Ala Lys Thr Val Lys Arg Phe

Figure 1g

Arg Glu Leu Asn Ile Gln Gly Gln Ile Ala Phe Lys Ser Asp Asn Phe
Val Gly Ile Pro Trp Arg Glu Gly Asn Gln Glu Asp Ile Asp Ala Val
Glu Arg His Gln Ala Tyr Gln Ile Gly Ile Phe Ala Glu Pro Ile Tyr
Asn Thr Gly Asp Trp Pro Asp Ile Val Lys Asn Asp Leu Ser Pro Asp
Ile Leu Pro Arg Phe Thr Asp Asp Glu Ile Ala Met Ile Lys Cys Thr
Ala Asp Phe Phe Pro Ile Asp Gly Tyr Arg Asp Gly Tyr Val Gln Ala
Val Pro Gly Gly Val Glu Ala Cys Val Ala Asn Ile Ser Asn Pro Leu
Trp Pro Ala Cys Asn Gln Val Asn Phe Tyr Asp Ser Thr Pro Ala Gly
Trp Ala Ile Gly Thr Phe Gly Asn Trp Pro Thr Thr Pro Trp Leu Gln
Asn Thr Trp Gln Phe Val Arg Pro Phe Leu Ala Asp Leu Ala Lys Arg
Tyr Pro Thr Glu Gly Gly Ile Tyr Leu Ser Glu Phe Gly Phe Ser Glu
Pro Phe Glu Asn Asp Lys Thr Phe Ile Tyr Gln Ile Thr Gln Asp Ser
Gly Arg Thr Ala Tyr Phe Asn Ser Tyr Leu Gly Glu Val Leu Lys Gly
Ile Val Glu Asp Gly Ile Pro Ile Lys Gly Val Phe Gly Trp Ser Met
Val Asp Asn Phe Glu Trp Asn Ser Gly Leu Ser Thr Arg Phe Gly Val
Gln Tyr Val Asp Tyr Asn Ser Pro Thr Arg Gln Arg Thr Phe Lys Arg
Ser Ala Leu Glu Met Ser Glu Phe Trp Asn Ala His Arg Cys Ser Ala

Figure 1h

Ala Thr Gly Pro Val Gly Gly Gln Gly Thr Pro Ala Val Asn Phe Thr

Asp Tyr Ser Ser Ser Ser Leu Glu Gln Phe Trp Asn Asp Trp Val Gly

Glu Val Glu Glu Pro Pro Phe Ala Tyr Val Pro Glu Pro Pro Asn Pro

Tyr Pro Leu Pro Asn Ala Pro Pro Pro Ile Tyr Pro Glu Tyr Tyr Thr

Lys Arg Pro Lys Asp Ile Leu Pro Asp Tyr Lys Phe Pro Lys Asp Phe

Leu Phe Gly Trp Ala Thr Ala Ala Gln Gln Trp Glu Gly Ala Val Lys

Ala Asp Gly Lys Gly Pro Ser Ile Trp Asp Trp Ala Ser Arg Phe Pro

Gly Phe Ile Ala Asp Asn Thr Thr Ser Asp Val Gly Asp Leu Gly Tyr

Tyr Leu Tyr Lys Glu Asp Leu Ala Arg Ile Ala Ala Leu Gly Ala Asn

Val Tyr Ser Phe Ser Met Phe Trp Thr Arg Ile Phe Pro Phe Gly Lys

Ala Asp Ser Pro Val Asn Gln Ala Gly Ile Asp Phe Tyr His Asp Leu

Ile Asp Tyr Ser Trp Ser Leu Gly Ile Glu Pro Val Val Thr Leu Phe

His Trp Asp Thr Pro Leu Ala Leu Gln Leu Glu Tyr Gly Gly Phe Ala

Ser Glu Arg Ile Ile Asp Asp Tyr Val Asn Tyr Ala Glu Thr Val Phe

Lys Ala Tyr Asn Gly Ser Val His Lys Trp Val Thr Phe Asn Glu Pro

Val Val Phe Cys Ser Gln Met Ala Ala Pro Val Asn Thr Thr Leu Pro

Pro Asn Leu Asn Ser Thr Ile Tyr Pro Tyr Thr Cys Ser Tyr His Leu

Val Leu Ala His Ala Lys Thr Val Lys Arg Phe Arg Glu Leu Asn Ile

Figure 1i

Gln Gly Gln Ile Ala Phe Lys Ser Asp Asn Phe Val Gly Ile Pro Trp
Arg Glu Gly Asn Gln Glu Asp Ile Asp Ala Val Glu Arg His Gln Ala
Tyr Gln Ile Gly Ile Phe Ala Glu Pro Ile Tyr Asn Thr Gly Asp Trp
Pro Asp Ile Val Lys Asn Asp Leu Ser Pro Asp Ile Leu Pro Arg Phe
Thr Asp Asp Glu Ile Ala Met Ile Lys Cys Thr Ala Asp Phe Phe Pro
Ile Asp Gly Tyr Arg Asp Gly Tyr Val Gln Ala Val Pro Gly Gly Val
Glu Ala Cys Val Ala Asn Ile Ser Asn Pro Leu Trp Pro Ala Cys Asn
Gln Val Asn Phe Tyr Asp Ser Thr Pro Ala Gly Trp Ala Ile Gly Thr
Phe Gly Asn Trp Pro Thr Thr Pro Trp Leu Gln Asn Thr Trp Gln Phe
Val Arg Pro Phe Leu Ala Asp Leu Ala Lys Arg Tyr Pro Thr Glu Gly
Gly Ile Tyr Leu Ser Glu Phe Gly Phe Ser Glu Pro Phe Glu Asn Asp
Lys Thr Phe Ile Tyr Gln Ile Thr Gln Asp Ser Gly Arg Thr Ala Tyr
Phe Asn Ser Tyr Leu Gly Glu Val Leu Lys Gly Ile Val Glu Asp Gly
Ile Pro Ile Lys Gly Val Phe Gly Trp Ser Met Val Asp Asn Phe Glu
Trp Asn Ser Gly Leu Ser Thr Arg Phe Gly Val Gln Tyr Val Asp Tyr
Asn Ser Pro Thr Arg Gln Arg Thr Phe Lys Arg Ser Ala Leu Glu Met
Ser Glu Phe Trp Asn Ala His Arg Cys Ser Ala

SEQUENCE LISTING

```
<160> NUMBER OF SEQ ID NOS: 16

<210> SEQ ID NO 1
<211> LENGTH: 696
<212> TYPE: PRT
<213> ORGANISM: Cryptococcus terrestris

<400> SEQUENCE: 1

Met Ile Pro Ala Ser Ala Leu Leu Ala Ala Val Pro Leu Leu Ala Gln
1               5                   10                  15

Gln Val Ser Ala Gly Ile Leu Arg Arg Gln Asn Ala Ala Gly Ser Asp
            20                  25                  30

Ser Ala Ala Pro Asp Ser Ile Ala Asp Ala Ser Thr Gly Val Val Ser
        35                  40                  45

Ser Ile Ala Thr Glu Ala Val Ser Ser Gly Ala Thr Gly Leu Val Ala
    50                  55                  60
```

```
Ser Val Ala Met Ser Phe Ala Ser Ser Met Ala Thr Pro Thr Ala Thr
 65                  70                  75                  80

Val Thr Gly Leu Ser Ser Glu Thr Gly Ala Pro Ser Asn Thr Pro Met
                 85                  90                  95

Ala Ser Ala Ser Gly Ser Val Pro Thr Thr Ser Ala Val Gly Ser
            100                 105                 110

Gly Asp Phe Asp Trp Val Gln Thr Asp Gly Leu Pro Thr Ile Thr Thr
            115                 120                 125

Thr Leu Ala Thr Thr Asn Gln Asp Ala Ile Thr Pro Thr Ala Thr Gly
130                 135                 140

Pro Val Gly Gly Gln Gly Thr Pro Ala Val Asn Phe Thr Asp Tyr Ser
145                 150                 155                 160

Ser Ser Ser Leu Glu Gln Phe Trp Asn Asp Trp Val Gly Glu Val Glu
                165                 170                 175

Glu Pro Pro Phe Ala Tyr Val Pro Glu Pro Asn Pro Tyr Pro Leu
            180                 185                 190

Pro Asn Ala Pro Pro Ile Tyr Pro Glu Tyr Tyr Thr Lys Arg Pro
            195                 200                 205

Lys Asp Ile Leu Pro Asp Tyr Lys Phe Pro Lys Asp Phe Leu Phe Gly
210                 215                 220

Trp Ala Thr Ala Ala Gln Gln Trp Glu Gly Ala Val Lys Ala Asp Gly
225                 230                 235                 240

Lys Gly Pro Ser Ile Trp Asp Trp Ala Ser Arg Phe Pro Gly Phe Ile
                245                 250                 255

Ala Asp Asn Thr Thr Ser Asp Val Gly Asp Leu Gly Tyr Tyr Leu Tyr
            260                 265                 270

Lys Glu Asp Leu Ala Arg Ile Ala Ala Leu Gly Ala Asn Val Tyr Ser
            275                 280                 285

Phe Ser Met Phe Trp Thr Arg Ile Phe Pro Phe Gly Lys Ala Asp Ser
290                 295                 300

Pro Val Asn Gln Ala Gly Ile Asp Phe Tyr His Asp Leu Ile Asp Tyr
305                 310                 315                 320

Ser Trp Ser Leu Gly Ile Glu Pro Val Val Thr Leu Phe His Trp Asp
                325                 330                 335

Thr Pro Leu Ala Leu Gln Leu Glu Tyr Gly Gly Phe Ala Ser Glu Arg
            340                 345                 350

Ile Ile Asp Asp Tyr Val Asn Tyr Ala Glu Thr Val Phe Lys Ala Tyr
            355                 360                 365

Asn Gly Ser Val His Lys Trp Val Thr Phe Asn Glu Pro Val Val Phe
370                 375                 380

Cys Ser Gln Met Ala Ala Pro Val Asn Thr Thr Leu Pro Pro Asn Leu
385                 390                 395                 400

Asn Ser Thr Ile Tyr Pro Tyr Thr Cys Ser Tyr His Leu Val Leu Ala
                405                 410                 415

His Ala Lys Thr Val Lys Arg Phe Arg Glu Leu Asn Ile Gln Gly Gln
            420                 425                 430

Ile Ala Phe Lys Ser Asp Asn Phe Val Gly Ile Pro Trp Arg Glu Gly
            435                 440                 445

Asn Gln Glu Asp Ile Asp Ala Val Glu Arg His Gln Ala Tyr Gln Ile
            450                 455                 460

Gly Ile Phe Ala Glu Pro Ile Tyr Asn Thr Gly Asp Trp Pro Asp Ile
465                 470                 475                 480
```

-continued

```
Val Lys Asn Asp Leu Ser Pro Asp Ile Leu Pro Arg Phe Thr Asp Asp
                485                 490                 495

Glu Ile Ala Met Ile Lys Cys Thr Ala Asp Phe Phe Pro Ile Asp Gly
            500                 505                 510

Tyr Arg Asp Gly Tyr Val Gln Ala Val Pro Gly Gly Val Glu Ala Cys
        515                 520                 525

Val Ala Asn Ile Ser Asn Pro Leu Trp Pro Ala Cys Asn Gln Val Asn
    530                 535                 540

Phe Tyr Asp Ser Thr Pro Ala Gly Trp Ala Ile Gly Thr Phe Gly Asn
545                 550                 555                 560

Trp Pro Thr Thr Pro Trp Leu Gln Asn Thr Trp Gln Phe Val Arg Pro
                565                 570                 575

Phe Leu Ala Asp Leu Ala Lys Arg Tyr Pro Thr Glu Gly Gly Ile Tyr
            580                 585                 590

Leu Ser Glu Phe Gly Phe Ser Glu Pro Phe Glu Asn Asp Lys Thr Phe
        595                 600                 605

Ile Tyr Gln Ile Thr Gln Asp Ser Gly Arg Thr Ala Tyr Phe Asn Ser
    610                 615                 620

Tyr Leu Gly Glu Val Leu Lys Gly Ile Val Glu Asp Gly Ile Pro Ile
625                 630                 635                 640

Lys Gly Val Phe Gly Trp Ser Met Val Asp Asn Phe Glu Trp Asn Ser
                645                 650                 655

Gly Leu Ser Thr Arg Phe Gly Val Gln Tyr Val Asp Tyr Asn Ser Pro
            660                 665                 670

Thr Arg Gln Arg Thr Phe Lys Arg Ser Ala Leu Glu Met Ser Glu Phe
        675                 680                 685

Trp Asn Ala His Arg Cys Ser Ala
    690                 695

<210> SEQ ID NO 2
<211> LENGTH: 566
<212> TYPE: PRT
<213> ORGANISM: Cryptococcus terrestris

<400> SEQUENCE: 2

Ala Thr Thr Asn Gln Asp Ala Ile Thr Pro Thr Ala Thr Gly Pro Val
1               5                   10                  15

Gly Gly Gln Gly Thr Pro Ala Val Asn Phe Thr Asp Tyr Ser Ser Ser
                20                  25                  30

Ser Leu Glu Gln Phe Trp Asn Asp Trp Val Gly Glu Val Glu Glu Pro
            35                  40                  45

Pro Phe Ala Tyr Val Pro Glu Pro Asn Pro Tyr Pro Leu Pro Asn
        50                  55                  60

Ala Pro Pro Pro Ile Tyr Pro Glu Tyr Tyr Thr Lys Arg Pro Lys Asp
65                  70                  75                  80

Ile Leu Pro Asp Tyr Lys Phe Pro Lys Asp Phe Leu Phe Gly Trp Ala
                85                  90                  95

Thr Ala Ala Gln Gln Trp Glu Gly Ala Val Lys Ala Asp Gly Lys Gly
            100                 105                 110

Pro Ser Ile Trp Asp Trp Ala Ser Arg Phe Pro Gly Phe Ile Ala Asp
        115                 120                 125

Asn Thr Thr Ser Asp Val Gly Asp Leu Gly Tyr Tyr Leu Tyr Lys Glu
    130                 135                 140

Asp Leu Ala Arg Ile Ala Ala Leu Gly Ala Asn Val Tyr Ser Phe Ser
145                 150                 155                 160
```

```
Met Phe Trp Thr Arg Ile Phe Pro Phe Gly Lys Ala Asp Ser Pro Val
                165                 170                 175

Asn Gln Ala Gly Ile Asp Phe Tyr His Asp Leu Ile Asp Tyr Ser Trp
            180                 185                 190

Ser Leu Gly Ile Glu Pro Val Val Thr Leu Phe His Trp Asp Thr Pro
        195                 200                 205

Leu Ala Leu Gln Leu Glu Tyr Gly Gly Phe Ala Ser Glu Arg Ile Ile
210                 215                 220

Asp Asp Tyr Val Asn Tyr Ala Glu Thr Val Phe Lys Ala Tyr Asn Gly
225                 230                 235                 240

Ser Val His Lys Trp Val Thr Phe Asn Glu Pro Val Val Phe Cys Ser
                245                 250                 255

Gln Met Ala Ala Pro Val Asn Thr Thr Leu Pro Pro Asn Leu Asn Ser
            260                 265                 270

Thr Ile Tyr Pro Tyr Thr Cys Ser Tyr His Leu Val Leu Ala His Ala
        275                 280                 285

Lys Thr Val Lys Arg Phe Arg Glu Leu Asn Ile Gln Gly Gln Ile Ala
    290                 295                 300

Phe Lys Ser Asp Asn Phe Val Gly Ile Pro Trp Arg Glu Gly Asn Gln
305                 310                 315                 320

Glu Asp Ile Asp Ala Val Glu Arg His Gln Ala Tyr Gln Ile Gly Ile
                325                 330                 335

Phe Ala Glu Pro Ile Tyr Asn Thr Gly Asp Trp Pro Asp Ile Val Lys
            340                 345                 350

Asn Asp Leu Ser Pro Asp Ile Leu Pro Arg Phe Thr Asp Glu Ile
        355                 360                 365

Ala Met Ile Lys Cys Thr Ala Asp Phe Phe Pro Ile Asp Gly Tyr Arg
    370                 375                 380

Asp Gly Tyr Val Gln Ala Val Pro Gly Gly Val Glu Ala Cys Val Ala
385                 390                 395                 400

Asn Ile Ser Asn Pro Leu Trp Pro Ala Cys Asn Gln Val Asn Phe Tyr
                405                 410                 415

Asp Ser Thr Pro Ala Gly Trp Ala Ile Gly Thr Phe Gly Asn Trp Pro
            420                 425                 430

Thr Thr Pro Trp Leu Gln Asn Thr Trp Gln Phe Val Arg Pro Phe Leu
        435                 440                 445

Ala Asp Leu Ala Lys Arg Tyr Pro Thr Glu Gly Ile Tyr Leu Ser
    450                 455                 460

Glu Phe Gly Phe Ser Glu Pro Phe Glu Asn Asp Lys Thr Phe Ile Tyr
465                 470                 475                 480

Gln Ile Thr Gln Asp Ser Gly Arg Thr Ala Tyr Phe Asn Ser Tyr Leu
                485                 490                 495

Gly Glu Val Leu Lys Gly Ile Val Glu Asp Gly Ile Pro Ile Lys Gly
            500                 505                 510

Val Phe Gly Trp Ser Met Val Asp Asn Phe Glu Trp Asn Ser Gly Leu
        515                 520                 525

Ser Thr Arg Phe Gly Val Gln Tyr Val Asp Tyr Asn Ser Pro Thr Arg
    530                 535                 540

Gln Arg Thr Phe Lys Arg Ser Ala Leu Glu Met Ser Glu Phe Trp Asn
545                 550                 555                 560

Ala His Arg Cys Ser Ala
                565
```

<210> SEQ ID NO 3
<211> LENGTH: 560
<212> TYPE: PRT
<213> ORGANISM: Cryptococcus terrestris

<400> SEQUENCE: 3

```
Ala Ile Thr Pro Thr Ala Thr Gly Pro Val Gly Gly Gln Gly Thr Pro
1               5                   10                  15

Ala Val Asn Phe Thr Asp Tyr Ser Ser Ser Leu Glu Gln Phe Trp
            20                  25                  30

Asn Asp Trp Val Gly Glu Val Glu Pro Pro Phe Ala Tyr Val Pro
                35                  40                  45

Glu Pro Pro Asn Pro Tyr Pro Leu Pro Asn Ala Pro Pro Ile Tyr
        50                  55                  60

Pro Glu Tyr Tyr Thr Lys Arg Pro Lys Asp Ile Leu Pro Asp Tyr Lys
65                  70                  75                  80

Phe Pro Lys Asp Phe Leu Phe Gly Trp Ala Thr Ala Ala Gln Gln Trp
                85                  90                  95

Glu Gly Ala Val Lys Ala Asp Gly Lys Gly Pro Ser Ile Trp Asp Trp
            100                 105                 110

Ala Ser Arg Phe Pro Gly Phe Ile Ala Asp Asn Thr Thr Ser Asp Val
        115                 120                 125

Gly Asp Leu Gly Tyr Tyr Leu Tyr Lys Glu Asp Leu Ala Arg Ile Ala
130                 135                 140

Ala Leu Gly Ala Asn Val Tyr Ser Phe Ser Met Phe Trp Thr Arg Ile
145                 150                 155                 160

Phe Pro Phe Gly Lys Ala Asp Ser Pro Val Asn Gln Ala Gly Ile Asp
                165                 170                 175

Phe Tyr His Asp Leu Ile Asp Tyr Ser Trp Ser Leu Gly Ile Glu Pro
            180                 185                 190

Val Val Thr Leu Phe His Trp Asp Thr Pro Leu Ala Leu Gln Leu Glu
        195                 200                 205

Tyr Gly Gly Phe Ala Ser Glu Arg Ile Ile Asp Asp Tyr Val Asn Tyr
210                 215                 220

Ala Glu Thr Val Phe Lys Ala Tyr Asn Gly Ser Val His Lys Trp Val
225                 230                 235                 240

Thr Phe Asn Glu Pro Val Val Phe Cys Ser Gln Met Ala Ala Pro Val
                245                 250                 255

Asn Thr Thr Leu Pro Pro Asn Leu Asn Ser Thr Ile Tyr Pro Tyr Thr
            260                 265                 270

Cys Ser Tyr His Leu Val Leu Ala His Ala Lys Thr Val Lys Arg Phe
        275                 280                 285

Arg Glu Leu Asn Ile Gln Gly Gln Ile Ala Phe Lys Ser Asp Asn Phe
290                 295                 300

Val Gly Ile Pro Trp Arg Glu Gly Asn Gln Glu Asp Ile Asp Ala Val
305                 310                 315                 320

Glu Arg His Gln Ala Tyr Gln Ile Gly Ile Phe Ala Glu Pro Ile Tyr
                325                 330                 335

Asn Thr Gly Asp Trp Pro Asp Ile Val Lys Asn Asp Leu Ser Pro Asp
            340                 345                 350

Ile Leu Pro Arg Phe Thr Asp Asp Glu Ile Ala Met Ile Lys Cys Thr
        355                 360                 365

Ala Asp Phe Phe Pro Ile Asp Gly Tyr Arg Asp Gly Tyr Val Gln Ala
370                 375                 380
```

Val Pro Gly Gly Val Glu Ala Cys Val Ala Asn Ile Ser Asn Pro Leu
385                 390                 395                 400

Trp Pro Ala Cys Asn Gln Val Asn Phe Tyr Asp Ser Thr Pro Ala Gly
            405                 410                 415

Trp Ala Ile Gly Thr Phe Gly Asn Trp Pro Thr Thr Pro Trp Leu Gln
        420                 425                 430

Asn Thr Trp Gln Phe Val Arg Pro Phe Leu Ala Asp Leu Ala Lys Arg
    435                 440                 445

Tyr Pro Thr Glu Gly Gly Ile Tyr Leu Ser Glu Phe Gly Phe Ser Glu
450                 455                 460

Pro Phe Glu Asn Asp Lys Thr Phe Ile Tyr Gln Ile Thr Gln Asp Ser
465                 470                 475                 480

Gly Arg Thr Ala Tyr Phe Asn Ser Tyr Leu Gly Glu Val Leu Lys Gly
            485                 490                 495

Ile Val Glu Asp Gly Ile Pro Ile Lys Gly Val Phe Gly Trp Ser Met
        500                 505                 510

Val Asp Asn Phe Glu Trp Asn Ser Gly Leu Ser Thr Arg Phe Gly Val
    515                 520                 525

Gln Tyr Val Asp Tyr Asn Ser Pro Thr Arg Gln Arg Thr Phe Lys Arg
530                 535                 540

Ser Ala Leu Glu Met Ser Glu Phe Trp Asn Ala His Arg Cys Ser Ala
545                 550                 555                 560

<210> SEQ ID NO 4
<211> LENGTH: 555
<212> TYPE: PRT
<213> ORGANISM: Cryptococcus terrestris

<400> SEQUENCE: 4

Ala Thr Gly Pro Val Gly Gly Gln Gly Thr Pro Ala Val Asn Phe Thr
1               5                   10                  15

Asp Tyr Ser Ser Ser Leu Glu Gln Phe Trp Asn Asp Trp Val Gly
            20                  25                  30

Glu Val Glu Glu Pro Pro Phe Ala Tyr Val Pro Glu Pro Asn Pro
        35                  40                  45

Tyr Pro Leu Pro Asn Ala Pro Pro Ile Tyr Pro Glu Tyr Tyr Thr
    50                  55                  60

Lys Arg Pro Lys Asp Ile Leu Pro Asp Tyr Lys Phe Pro Lys Asp Phe
65                  70                  75                  80

Leu Phe Gly Trp Ala Thr Ala Ala Gln Gln Trp Glu Gly Ala Val Lys
            85                  90                  95

Ala Asp Gly Lys Gly Pro Ser Ile Trp Asp Trp Ala Ser Arg Phe Pro
        100                 105                 110

Gly Phe Ile Ala Asp Asn Thr Thr Ser Asp Val Gly Asp Leu Gly Tyr
    115                 120                 125

Tyr Leu Tyr Lys Glu Asp Leu Ala Arg Ile Ala Ala Leu Gly Ala Asn
        130                 135                 140

Val Tyr Ser Phe Ser Met Phe Trp Thr Arg Ile Phe Pro Phe Gly Lys
145                 150                 155                 160

Ala Asp Ser Pro Val Asn Gln Ala Gly Ile Asp Phe Tyr His Asp Leu
            165                 170                 175

Ile Asp Tyr Ser Trp Ser Leu Gly Ile Glu Pro Val Val Thr Leu Phe
        180                 185                 190

His Trp Asp Thr Pro Leu Ala Leu Gln Leu Glu Tyr Gly Gly Phe Ala

-continued

```
                195                 200                 205
Ser Glu Arg Ile Ile Asp Asp Tyr Val Asn Tyr Ala Glu Thr Val Phe
210                 215                 220

Lys Ala Tyr Asn Gly Ser Val His Lys Trp Val Thr Phe Asn Glu Pro
225                 230                 235                 240

Val Val Phe Cys Ser Gln Met Ala Ala Pro Val Asn Thr Thr Leu Pro
                245                 250                 255

Pro Asn Leu Asn Ser Thr Ile Tyr Pro Tyr Thr Cys Ser Tyr His Leu
                260                 265                 270

Val Leu Ala His Ala Lys Thr Val Lys Arg Phe Arg Glu Leu Asn Ile
                275                 280                 285

Gln Gly Gln Ile Ala Phe Lys Ser Asp Asn Phe Val Gly Ile Pro Trp
290                 295                 300

Arg Glu Gly Asn Gln Glu Asp Ile Asp Ala Val Glu Arg His Gln Ala
305                 310                 315                 320

Tyr Gln Ile Gly Ile Phe Ala Glu Pro Ile Tyr Asn Thr Gly Asp Trp
                325                 330                 335

Pro Asp Ile Val Lys Asn Asp Leu Ser Pro Asp Ile Leu Pro Arg Phe
                340                 345                 350

Thr Asp Asp Glu Ile Ala Met Ile Lys Cys Thr Ala Asp Phe Phe Pro
                355                 360                 365

Ile Asp Gly Tyr Arg Asp Gly Tyr Val Gln Ala Val Pro Gly Gly Val
370                 375                 380

Glu Ala Cys Val Ala Asn Ile Ser Asn Pro Leu Trp Pro Ala Cys Asn
385                 390                 395                 400

Gln Val Asn Phe Tyr Asp Ser Thr Pro Ala Gly Trp Ala Ile Gly Thr
                405                 410                 415

Phe Gly Asn Trp Pro Thr Thr Pro Trp Leu Gln Asn Thr Trp Gln Phe
                420                 425                 430

Val Arg Pro Phe Leu Ala Asp Leu Ala Lys Arg Tyr Pro Thr Glu Gly
                435                 440                 445

Gly Ile Tyr Leu Ser Glu Phe Gly Phe Ser Glu Pro Phe Glu Asn Asp
450                 455                 460

Lys Thr Phe Ile Tyr Gln Ile Thr Gln Asp Ser Gly Arg Thr Ala Tyr
465                 470                 475                 480

Phe Asn Ser Tyr Leu Gly Glu Val Leu Lys Gly Ile Val Glu Asp Gly
                485                 490                 495

Ile Pro Ile Lys Gly Val Phe Gly Trp Ser Met Val Asp Asn Phe Glu
                500                 505                 510

Trp Asn Ser Gly Leu Ser Thr Arg Phe Gly Val Gln Tyr Val Asp Tyr
                515                 520                 525

Asn Ser Pro Thr Arg Gln Arg Thr Phe Lys Arg Ser Ala Leu Glu Met
                530                 535                 540

Ser Glu Phe Trp Asn Ala His Arg Cys Ser Ala
545                 550                 555
```

<210> SEQ ID NO 5
<211> LENGTH: 2091
<212> TYPE: DNA
<213> ORGANISM: Cryptococcus terrestris

<400> SEQUENCE: 5

```
atgatcccgg caagtgcact ccttgccgcc gtacccctcc ttgcccaaca ggtgagcgcc    60
ggcatactgc gaagacagaa tgctgcgggt tcggattcgg cagcgcctga ctcgatcgcg   120
```

-continued

```
gatgcgtcca ccggtgtcgt ctcgtcgatc gccacggaag ccgtctcttc gggagcgaca      180
ggccttgtcg cgtccgtcgc catgtcattc gcctcgtcga tggcgactcc aacggccaca      240
gtgacgggcc taagctccga cgggagcg ccttccaaca ccccaatggc cagtgcctct        300
ggtagtgtcc ctacaaccac ctctgccgtc gggtctggcg acttcgactg ggtccagaca      360
gacggcctgc ccacgatcac gaccactttg gctactacga accaggacgc aatcactccg      420
acggcgacgg gccccgtcgg cggacagggc acccctgctg tcaacttcac cgactactct     480
tcatcgtcgc tcgagcagtt ttggaacgac tgggtgggag aggtggagga gccgccgttc     540
gcctacgtcc cggaaccgcc taacccgtac ccgttaccga acgccccgcc tccaatctac      600
cccgagtact acaccaagcg tcccaaggac attctccccg actacaagtt ccccaaagac     660
ttcctgtttg gctgggcgac cgccgcgcag cagtgggagg gggccgtcaa ggcggatggg     720
aaggggccgt ccatctggga ctgggccagc cggttcccgg ggttcattgc ggacaacacg     780
acttccgacg tcgagacttt gggatactat ttatacaaag aggacctcgc taggatcgct      840
gcattgggcg caaacgttta ctctttcagc atgttctgga cacggatctt tccctttcggc    900 aaggccgact cgcctgtcaa tcaagcgggc atcgacttct accacgactt gatcgattat    960
tcttggagcc tgggcatcga gcccgtcgtg acattgttcc attgggatac gccgctcgcc    1020
ctccagcttg agtacggagg tttcgccagc gagcgaatca ttgatgacta cgtcaactat    1080
gcggaaaccg tgttcaaggc gtacaacggt agtgtgcaca aatgggtcac attcaacgag    1140
cctgtggtgt tctgcagcca gatggcagcg cccgtgaaca ctactctacc gccgaacctc    1200
aactcgacaa tctaccccta tacctgcagc tatcacctcg tgctagccca cgccaagacg    1260
gtcaagcggt tcagggagtt gaacattcag ggccagatcg cttttcaagtc ggacaatttt   1320 gtcggtatcc cgtggcgtga ggggaaccaa gaggacatag atgcggtcga cgccatcag    1380 gcgtaccaga tcgggatctt tgctgagccg atctacaaca ccggagactg gcccgatatc    1440
gtgaagaatg atctctcccc cgacatcctt cctcgattca cggatgacga gatcgcgatg    1500
atcaagtgca ctgccgactt cttcccatc gatggctaca gggacggtta tgtccaggct     1560
gtaccggggg gtgtcgaagc ttgcgtcgcg aacatcagca acccgctttg gcctgcttgc   1620
aaccaagtca acttctatga ttccacaccc gccggatggg cgatcggcac gttcggcaac   1680
tggccgacga caccctggct ccagaacacc tggcagtttg tgcgcccctt cctcgctgat   1740
ctggcaaagc ggtaccccac cgaaggcggc atctaccttt cggaatttgg cttctccgag   1800
ccgttcgaaa atgataaaac cttcatttac cagatcaccc aggacagcgg acggacggcg   1860
tacttcaaca gttacctcgg cgaagtgttg aaaggtatcg ttgaagatgg cattcctatc   1920
aagggcgtgt tcggctggag tatggtcgac aactttgaat ggaactctgg cttgtctact   1980
cgcttcggcg tccaatacgt tgattacaac agcccgacgc gtcaacgaac gttcaagcgg   2040
tccgctctgg agatgagcga gttctggaat gctcatcgat gttccgccta a             2091
```

<210> SEQ ID NO 6
<211> LENGTH: 1701
<212> TYPE: DNA
<213> ORGANISM: Cryptococcus terrestris

<400> SEQUENCE: 6

```
gctactacga accaggacgc aatcactccg acggcgacgg gccccgtcgg cggacagggc       60 accctgctg tcaacttcac cgactactct tcatcgtcgc tcgagcagtt ttggaacgac       120
```

-continued

```
tgggtgggag aggtggagga gccgccgttc gcctacgtcc cggaaccgcc taacccgtac     180
ccgttaccga acgccccgcc tccaatctac cccgagtact acaccaagcg tcccaaggac     240
attctccccg actacaagtt ccccaaagac ttcctgtttg gctgggcgac cgccgcgcag     300
cagtgggagg gggccgtcaa ggcggatggg aaggggccgt ccatctggga ctgggccagc     360
cggttcccgg ggttcattgc ggacaacacg acttccgacg tcggagactt gggatactat     420
ttatacaaag aggacctcgc taggatcgct gcattgggcg caaacgttta ctctttcagc     480
atgttctgga cacggatctt tcccttcggc aaggccgact cgcctgtcaa tcaagcgggc     540
atcgacttct accacgactt gatcgattat tcttggagcc tgggcatcga gcccgtcgtg     600
acattgttcc attgggatac gccgctcgcc ctccagcttg agtacggagg tttcgccagc     660
gagcgaatca ttgatgacta cgtcaactat gcggaaaccg tgttcaaggc gtacaacggt     720
agtgtgcaca aatgggtcac attcaacgag cctgtggtgt ctgcagcca gatggcagcg     780 cccgtgaaca ctactctacc gccgaacctc aactcgacaa tctacccta tacctgcagc     840 tatcacctcg tgctagccca cgccaagacg gtcaagcggt tcagggagtt gaacattcag     900
ggccagatcg ctttcaagtc ggacaatttt gtcggtatcc cgtggcgtga ggggaaccaa     960
gaggacatag atgcggtcga gcgccatcag gcgtaccaga tcgggatctt tgctgagccg    1020
atctacaaca ccggagactg gcccgatatc gtgaagaatg atctctcccc cgacatcctt    1080
cctcgattca cggatgacga gatcgcgatg atcaagtgca ctgccgactt cttccccatc    1140
gatggctaca gggacggtta tgtccaggct gtaccggggg gtgtcgaagc ttgcgtcgcg    1200
aacatcagca cccgctttg gcctgcttgc aaccaagtca acttctatga ttccacaccc    1260
gccggatggg cgatcggcac gttcggcaac tggccgacga caccctggct ccagaacacc    1320
tggcagtttg tgcgcccctt cctcgctgat ctggcaaagc ggtaccccac cgaaggcggc    1380
atctaccttt cggaatttgg cttctccgag ccgttcgaaa atgataaaac cttcatttac    1440
cagatcaccc aggacagcgg acggacggcg tacttcaaca gttacctcgg cgaagtgttg    1500
aaaggtatcg ttgaagatgg cattcctatc aagggcgtgt tcggctggag tatggtcgac    1560
aactttgaat ggaactctgg cttgtctact cgcttcggcg tccaatacgt tgattacaac    1620
agcccgacgc gtcaacgaac gttcaagcgg tccgctctgg agatgagcga gttctggaat    1680
gctcatcgat gttccgccta a                                              1701
```

<210> SEQ ID NO 7
<211> LENGTH: 1683
<212> TYPE: DNA
<213> ORGANISM: Cryptococcus terrestris

<400> SEQUENCE: 7

```
gcaatcactc cgacggcgac gggccccgtc ggcggacagg gcacccctgc tgtcaacttc      60
accgactact cttcatcgtc gctcgagcag ttttggaacg actgggtggg agaggtggag     120
gagccgccgt tcgcctacgt cccggaaccg cctaacccgt accgttacc gaacgccccg     180 cctccaatct accccgagta ctacaccaag cgtcccaagg acattctccc cgactacaag     240
ttccccaaag acttcctgtt tggctgggcg accgccgcgc agcagtggga ggggccgtc     300 aaggcggatg ggaaggggcc gtccatctgg gactgggcca gccggttccc ggggttcatt     360
gcggacaaca cgacttccga cgtcggagac ttgggatact atttatacaa agaggacctc     420
gctaggatcc tgcattggg cgcaaacgtt tactctttca gcatgttctg gacacggatc     480
tttcccttcg gcaaggccga ctcgcctgtc aatcaagcgg gcatcgactt ctaccacgac     540
```

```
ttgatcgatt attcttggag cctgggcatc gagcccgtcg tgacattgtt ccattgggat      600
acgccgctcg ccctccagct tgagtacgga ggtttcgcca gcgagcgaat cattgatgac      660
tacgtcaact atgcggaaac cgtgttcaag gcgtacaacg gtagtgtgca caaatgggtc      720
acattcaaca gcctgtggt gttctgcagc cagatggcag cgcccgtgaa cactactcta       780
ccgccgaacc tcaactcgac aatctacccc tatacctgca gctatcacct cgtgctagcc      840
cacgccaaga cggtcaagcg gttcagggag ttgaacattc agggccagat cgctttcaag      900
tcggacaatt ttgtcggtat cccgtggcgt gaggggaacc aagaggacat agatgcggtc      960
gagcgccatc aggcgtacca gatcgggatc tttgctgagc cgatctacaa caccggagac     1020
tggcccgata tcgtgaagaa tgatctctcc cccgacatcc ttcctcgatt cacggatgac     1080
gagatcgcga tgatcaagtg cactgccgac ttcttcccca tcgatggcta cagggacggt     1140
tatgtccagg ctgtaccggg gggtgtcgaa gcttgcgtcg cgaacatcag caacccgctt     1200
tggcctgctt gcaaccaagt caacttctat gattccacac ccgccggatg ggcgatcggc     1260
acgttcggca actggccgac gacaccctgg ctccagaaca cctggcagtt tgtgcgcccc     1320
ttcctcgctg atctggcaaa gcggtacccc accgaaggcg gcatctacct ttcggaattt     1380
ggcttctccg agccgttcga aaatgataaa accttcattt accagatcac ccaggacagc     1440
ggacggacgg cgtacttcaa cagttacctc ggcgaagtgt tgaaaggtat cgttgaagat     1500
ggcattccta tcaagggcgt gttcggctgg agtatggtcg acaactttga atggaactct     1560
ggcttgtcta ctcgcttcgg cgtccaatac gttgattaca cagcccgac gcgtcaacga      1620 acgttcaagc ggtccgctct ggagatgagc gagttctgga atgctcatcg atgttccgcc     1680
taa                                                                   1683

<210> SEQ ID NO 8
<211> LENGTH: 1668
<212> TYPE: DNA
<213> ORGANISM: Cryptococcus terrestris

<400> SEQUENCE: 8
gcgacgggcc ccgtcggcgg acagggcacc cctgctgtca acttcaccga ctactcttca       60
tcgtcgctcg agcagttttg gaacgactgg gtgggagagg tggaggagcc gccgttcgcc      120
tacgtcccgg aaccgcctaa cccgtacccg ttaccgaacg ccccgcctcc aatctacccc      180
gagtactaca ccaagcgtcc caaggacatt ctccccgact acaagttccc caaagacttc      240
ctgtttggct gggcgaccgc cgcgcagcag tgggaggggg ccgtcaaggc ggatgggaag      300
gggccgtcca tctgggactg gccagccggt tcccgggggt tcattgcgga caacacgact      360
tccgacgtcg gagacttggg atactattta tacaaagagg acctcgctag gatcgctgca      420
ttgggcgcaa acgtttactc tttcagcatg ttctggacac ggatctttcc cttcggcaag      480
gccgactcgc ctgtcaatca gcgggcatc gacttctacc acgacttgat cgattattct       540
tggagcctgg gcatcgagcc cgtcgtgaca ttgttccatt gggatacgcc gctcgccctc      600
cagcttgagt acgaaggttt cgccagcgag cgaatcattg atgactacgt caactatgcg      660
gaaaccgtgt tcaaggcgta caacggtagt gtgcacaaat gggtcacatt caacgagcct      720
gtggtgttct gcagccagat ggcagcgccc gtgaacacta ctctaccgcc gaacctcaac      780
tcgacaatct accctatac ctgcagctat cacctcgtgc tagcccacgc caagacggtc       840
aagcggttca gggagttgaa cattcagggc cagatcgctt tcaagtcgga caattttgtc     900
```

```
ggtatcccgt ggcgtgaggg gaaccaagag gacatagatg cggtcgagcg ccatcaggcg      960
taccagatcg ggatctttgc tgagccgatc tacaacaccg gagactggcc cgatatcgtg     1020
aagaatgatc tctcccccga catccttcct cgattcacgg atgacgagat cgcgatgatc     1080
aagtgcactg ccgacttctt ccccatcgat ggctacaggg acggttatgt ccaggctgta     1140
ccggggggtg tcgaagcttg cgtcgcgaac atcagcaacc cgctttggcc tgcttgcaac     1200
caagtcaact tctatgattc cacacccgcc ggatgggcga tcggcacgtt cggcaactgg     1260
ccgacgacac cctggctcca gaacacctgg cagtttgtgc gccccttcct cgctgatctg     1320
gcaaagcggt accccaccga aggcggcatc tacctttcgg aatttggctt ctccgagccg     1380
ttcgaaaatg ataaaacctt catttaccag atcacccagg acagcggacg gacggcgtac     1440
ttcaacagtt acctcggcga agtgttgaaa ggtatcgttg aagatggcat tcctatcaag     1500
ggcgtgttcg gctggagtat ggtcgacaac tttgaatgga actctggctt gtctactcgc     1560
ttcggcgtcc aatacgttga ttacaacagc ccgacgcgtc aacgaacgtt caagcggtcc     1620
gctctggaga tgagcgagtt ctggaatgct catcgatgtt ccgcctaa                  1668
```

<210> SEQ ID NO 9
<211> LENGTH: 11
<212> TYPE: PRT
<213> ORGANISM: Cryptococcus terrestris

<400> SEQUENCE: 9

Gly Val Gln Tyr Val Asp Tyr Asn Ser Pro Thr
1               5                   10

<210> SEQ ID NO 10
<211> LENGTH: 11
<212> TYPE: PRT
<213> ORGANISM: Cryptococcus terrestris

<400> SEQUENCE: 10

Phe Leu Phe Gly Trp Ala Thr Ala Ala Gln Gln
1               5                   10

<210> SEQ ID NO 11
<211> LENGTH: 15
<212> TYPE: PRT
<213> ORGANISM: Cryptococcus terrestris

<400> SEQUENCE: 11

Gln Ala Tyr Gln Ile Gly Ile Phe Ala Glu Pro Ile Tyr Asn Thr
1               5                   10                  15

<210> SEQ ID NO 12
<211> LENGTH: 8
<212> TYPE: PRT
<213> ORGANISM: Cryptococcus terrestris

<400> SEQUENCE: 12

Pro Ser Ile Trp Asp Trp Ala Ser
1               5

<210> SEQ ID NO 13
<211> LENGTH: 10
<212> TYPE: PRT
<213> ORGANISM: Cryptococcus terrestris

<400> SEQUENCE: 13

Glu Glu Pro Pro Phe Ala Tyr Val Pro Glu

<210> SEQ ID NO 14
<211> LENGTH: 41
<212> TYPE: DNA
<213> ORGANISM: Artificial Sequence
<220> FEATURE:
<223> OTHER INFORMATION: 5'RACE GSP primer

<400> SEQUENCE: 14
gattacgcca agcttgcaaa gatcccgatc tggtacgcct g            41

<210> SEQ ID NO 15
<211> LENGTH: 39
<212> TYPE: DNA
<213> ORGANISM: Artificial Sequence
<220> FEATURE:
<223> OTHER INFORMATION: 3'RACE GSP primer

<400> SEQUENCE: 15
gattacgcca agcttttcct gtttggctgg gcgaccgcc              39

<210> SEQ ID NO 16
<211> LENGTH: 2942
<212> TYPE: DNA
<213> ORGANISM: Cryptococcus terrestris

<400> SEQUENCE: 16

| | | |
|---|---|---|
| atgatcccgg caagtgcact ccttgccgcc gtacccctcc ttgcccaaca ggtgagcgcc | 60 |
| ggcatactgc gaagacagaa tgctgcgggt tcggattcgg cagcgcctga ctcgatcgcg | 120 |
| gatgcgtcca ccggtgtcgt ctcgtcgatc gccacggaag ccgtctcttc gggagcgaca | 180 |
| ggccttgtcg cgtccgtcgc catgtcattc gcctcgtcga tggcgactcc aacggccaca | 240 |
| gtgacgggcc taagctccga cgggagcg ccttccaaca ccccaatggc cagtgcctct | 300 |
| ggtagtgtcc ctacaaccac ctctgccgtc ggtctggcg acttcgactg gtccagaca | 360 |
| gacggcctgc ccacgatcac gaccactttg gctactacga accaggacgc aatcactccg | 420 |
| acggcgacgg gccccgtcgg cggacagggc acccctgctg tcaacttcac cgactactct | 480 |
| tcatcgtcgc tcgagcagtt ttggaacgac tgggtaagtt aggccacggc tccatctgct | 540 |
| gacgagggtc caggagagct gacgcacagg tgggagaggt ggaggagccg ccgttcgcct | 600 |
| acgtcccgga accgcctaac ccgtacccgt taccgaacgc cccgcctcca atctaccccg | 660 |
| agtactacac caagcgtccc aaggacattc tccccgacta caagttcccc aaagacttcc | 720 |
| tgtttggctg ggcgaccgcc gcgcagcagt gggaggggc cgtcaaggcg gatgggaagg | 780 |
| ggccgtccat ctgggactgg gccagccggt tcccggggtt cattgcggac aacacgactt | 840 |
| ccggtgagct gagaatgacc acctttcagt acgagagctc acttcagacg tcggagactt | 900 |
| gggatactat ttatacaaag agggttagcc ggggccgtat gagccagtgc tggatgctga | 960 |
| gtgcagacct cgctaggatc gctgcattgg gcgcaaacgt ttactctttc agcatgttct | 1020 |
| ggacacggat ctttcccttc ggcaaggccg actcgcctgt caatcaagcg gcatcgact | 1080 |
| tctaccacga cttgatcgat tattcttgga gcctgggcat cgagcccgtc gtgtaagcct | 1140 |
| gtacaggggc ccatcttgaa ccccgctcat tacaggacat tgttccattg ggatacgccg | 1200 |
| ctcgcccctcc agcttgagta cggaggtttc gccagcgagc gaatcattga tgactacgtc | 1260 |
| aactatgcgt tgagcagtac ggtcccttga gcacagcttg gctgactcg taaggaaacc | 1320 |
| gtgttcaagg cgtacaacgg tagtgtgcac aaatgggtca cattcaacga gcctgtggtg | 1380 |

-continued

```
ttctgcagcc aggtgagcaa ccaaagcgca tgttgagctg atcgaccaga tggcagcgcc    1440
cgtgaacgta agatgagcaa cgagccagac cagtgtcaat gctgaccatg accgtagact    1500
actctaccgc cgaacctcaa ctcgacaatc taccnctata cctgcagcta tcacctcgtg    1560
ctagcccacg ccaagacggt caagcggttc agggagttga acattcgtga gctgatcggt    1620
accgcgtttc tggctgaaga cacgctgact gtcacagagg gccagatcgc tttcaagtcg    1680
gacaattttg tgtgagcatc gctgttgtgg ggagtcgtgc gtgctgaacc tttagcggta    1740
tcccgtggcg tgagggaac caagaggaca tagatgcggt cgagcgccat caggtgaagt     1800
ctcgccagac cgcggaggct ccgaggctga ccggacaggc gtaccagatc gggatctttg    1860
ctgagccgat ctacaacacc ggagtgaggc ttccctccct cttccgcacg gtacacttgt    1920
ggcttatcga caggactggc ccgatatcgt gaagaatgat ctctcccccg acatccttcc    1980
tcgattcacg gatgacgaga tcgcgatgat caagtgcact gccgacttct tccccatcga    2040
tgtgagcctc caaacccacc cgtcgggaga cgggtcccga gtactacgcc taacgcacag    2100
ggctacaggg acggttatgt ccaggctgta ccgggggggtg tcgaagcttg cgtcgcgaac    2160
atcagcaacc cgctttggcc tgcttgcaac caagtcaagt gagactcgtc cagacccccgc   2220 ctgtattgcg agcgccggca ctgacatgca gcttctgtac ggcccacagc accccgtcgc    2280
cgccgctgag ctgatgcata gatgattcca cacccgccgg atgggcgatc ggcacgttcg    2340
gcaactggcc gacgacaccc tggctccaga acacctggca gtttgtgcgc cccttcctcg    2400
ctgatctggc aaagcggtac cccaccgaag gcggcatcta cctttcggaa tttggcttct    2460
ccgagccgtt cgaaaatgag tacgcctatc aactggctgc tgcaaggcat ggcgtactga    2520
gactcagtaa aaccttcatt taccagatca cccaggacag cggacggacg gcgtacttca    2580
acagttacct cggcgaagtg ttgaaaggta tcgttgaaga tggcattcct atcaagggcg    2640
tgttcggctg gagtatggtc gacaactttg aatggaactc tggcttgtct agtacgtcca    2700
cacggccgtg gatccttcga cgcccggtct gacccgtagc tcgcttcggc gtccaatacg    2760
ttgattacaa caggtgagct gtcgtttttg ttttagggat cgcgatgctg atgcaaacag    2820
cccgacgcgt caacgaacgg tacgccgttc atgacctccc cctcgtccct gctgacgtcc    2880
agttcaagcg gtccgctctg gagatgagcg agttctggaa tgctcatcga tgttccgcct    2940
aa                                                                   2942
```

METHOD FOR PREPARING GOS HAVING REDUCED ALLERGENICITY

CROSS-REFERENCE TO RELATED APPLICATIONS

The present application is a Continuation of International Patent Application No. PCT/EP2018/067134, filed Jun. 26, 2018, and claims the benefit of priority to European Patent Application No. 17178462.2, filed on Jun. 28, 2017, the entire contents of which are hereby incorporated by reference.

SEQUENCE LISTING

The instant application contains a Sequence Listing which has been submitted in ASCII and PDF format via EFS-WEB and is hereby incorporated by reference in its entirety.

TECHNICAL FIELD OF THE INVENTION

The invention relates to the field of nutritional ingredients. More in particular, it relates to methods for producing hypoallergenic galacto-oligosaccharides and the use thereof in food and drink items. The invention particularly relates to the use of a beta-galactosidase derived from *Cryptococcus terrestris* (recently renamed *Papiliotrema terrestris*) in the production of a hypoallergenic GOS preparation.

BACKGROUND OF THE INVENTION

The term "GOS" stands for galacto-oligosaccharides (GOS), which generally comprise a chain of galactose units and a terminal glucose unit, that arise through consecutive transgalactosylation reactions (transgalactosylation reactions), catalyzed by a beta-galactosidase. Some of the GOS components exist naturally in human breast milk and bovine colostrum. Typical GOS preparations mainly comprise di- to hexa-saccharides.

Various physiological functions of GOS have been reported, including the capacity to stimulate the growth of bifidogenic bacteria in the gut [1-3], to support normal gut transit [4], to contribute to natural defenses [5,6] and to enhance mineral absorption [7]. GOS has received particular attention for their prebiotic effects that promote the growth of *Bifidobacterium*, *Lactobacillus*, and other enteric bacteria. Therefore, GOS is commonly used in infant formula, beverages fermented by *Lactobacillus*, and yogurts. Some of these foods containing GOS are certified as Food for Specified Health Uses by the Consumer Affairs Agency in Japan, and GOS is certified as generally recognized as safe (GRAS) substances by the U.S. Food and Drug Administration (GRAS Notices: GRN 233, 236, 285, 286, 334, 484, 489, 495, 518, and 569).

In general, GOS is produced by a transglycosylation reaction (in particular a transgalactosylation reaction) with a beta-galactosidase enzyme (enzyme class EC.3.2.1.23). beta-Galactosidase enzymes are produced in many microorganisms such as *Bacillus circulans, Aspergillus oryzae, Kluyveromyces marxianus, Kluyveromyces fragilis, Sporobolomyces singularis*, and *Lactobacillus fermentum*. Beta-galactosidases differ in their three-dimensional structures, resulting in stereo- and regioselectivity of the glycosidic bonds that are formed. For example, typically a fungal beta-galactosidase derived from *Aspergillus* predominantly produces β1-6 bonds (thus resulting in a GOS preparation that predominantly comprises β1-6 bonds, which may be referred to as "6'-GOS"), while a bacterial beta-galactosidase derived from *Bacillus* predominantly produce β1-4 bonds (resulting in a GOS preparation that predominantly comprises β1-4 bonds, which may also be referred to as "4'-GOS"). Moreover, beta-galactosidase produced by *B. circulans* possesses particularly strong transgalactosylation activity, and thus, GOS prepared by *B. circulans* is sold worldwide.

Since its introduction to the market (1999), approximately more than 100 million of infants have consumed infant formula containing GOS prepared by *B. circulans*. It has been proven to be a safe ingredient, with a GRAS status acknowledged by the FDA.

In the past few years, however, a small number of very rare cases of GOS-related allergy has been reported in South East Asia. Research has shown that certain oligosaccharide structures present in GOS can exert an allergic response in very sensitive subjects [8].

Jyo et al. (Occup. Environ. Allergy 3, 12-20 (1992)) determined allergy symptoms after consumption of a *lactobacillus* beverage containing 6'-GOS produced by fungal beta-galactosidase. Allergy symptoms have also been observed with 4'-GOS produced by bacterial beta-galactosidase. In 2014, Kaneko et al. (Biosc. Biotechnol. Biochem. 78, 100-108) observed that GOS produced by treating lactose with a beta-galactosidase derived from *B. circulans* may induce allergic reactions and revealed that the allergies were caused by two tetrasaccharides [Gal β1-4 (Gal β1-4 Gal β1-6) Glc, Gal β1-4 Gal β1-4 Gal β1-3 Glc]. These GOS allergy cases occurred in subjects who already had a history of atopy.

The present inventors aimed at the manufacture of a GOS preparation having reduced allergenicity. In particular, they sought to identify a beta-galactosidase for use in the manufacture of a GOS preparation having a reduced capacity to induce an allergic response in a subject, as compared to a GOS preparation obtained by *Bacillus circulans* beta-galactosidase or by *Aspergillus oryzae* beta-galactosidase.

SUMMARY OF THE INVENTION

It was surprisingly observed that a GOS preparation produced by a β-galactosidase derived from a microorganism of the genus *Cryptococcus* has an unexpected low allergenicity. More specifically, it was found in an oral challenge test that GOS obtained using a *Cryptococcus terrestris* beta-galactosidase enzyme did not induce allergic symptoms in human subjects suffering from hypersensitivity to GOS prepared by conventional *B. circulans* enzyme.

Herewith, the invention provides the use of a beta-galactosidase (EC 3.2.1.23) derived from *C. terrestris* in the production of a hypoallergenic galacto-oligosaccharide (GOS) preparation. Said hypoallergenic GOS preparation has a reduced capacity to induce an (IgE-mediated) allergic response in a subject, as compared to a GOS preparation obtained by transgalactosylation of lactose using beta-galactosidase derived from *Bacillus circulans* or *Aspergillus oryzae*. More in particular, the said hypoallergenic GOS preparation has a reduced capacity to induce an (IgE-mediated) allergic response in a subject having an increased chance to suffering from hypersensitivity to a GOS preparation obtained by transgalactosylation of lactose using beta-galactosidase derived from *Bacillus circulans* or *Aspergillus oryzae*.

The invention also relates to a hypoallergenic GOS preparation obtainable by transgalactosylation of lactose using a beta-galactosidase (EC 3.2.1.23) derived from *Cryptococcus*

*terrestris* (recently renamed *Papiliotrema terrestris*), for use in at least partially preventing an (IgE-mediated) allergic response in a subject.

The invention also relates to a hypoallergenic GOS preparation obtainable by transgalactosylation of lactose using a beta-galactosidase (EC 3.2.1.23) derived from *Cryptococcus terrestris* (recently renamed *Papiliotrema terrestris*), for use in at least partially preventing an (IgE-mediated) allergic response in a subject known to suffer or having an increased chance to suffer from hypersensitivity to a GOS preparation obtained by transgalactosylation of lactose using a beta-galactosidase derived from *Bacillus circulans* or from *Aspergillus oryzae*.

The invention further relates to a hypoallergenic GOS preparation obtainable by transgalactosylation of lactose using a beta-galactosidase (EC 3.2.1.23) derived from *Cryptococcus terrestris* for use in a nutritional composition for a subject known to suffer or having an increased chance to suffer from hypersensitivity to a GOS preparation obtained by transgalactosylation of lactose using *Bacillus circulans* or *Aspergillus oryzae*.

The invention also provides a method for at least partially preventing hypersensitivity to a GOS preparation in a subject, comprising administering a (hypoallergenic) nutritional composition comprising a hypoallergenic GOS preparation obtainable by transgalactosylation of lactose using a beta-galactosidase (EC 3.2.1.23) derived from *Cryptococcus terrestris* (recently renamed *Papiliotrema terrestris*) to the subject.

The invention further provides a nutritional composition comprising (i) a hypoallergenic GOS preparation obtainable by transgalactosylation of lactose using a beta-galactosidase (EC 3.2.1.23) derived from *Cryptococcus terrestris* and (ii) at least one further ingredient selected from the group consisting of a hypoallergenic or non-allergenic protein source, preferably a protein hydrolysate, preferably a non-allergenic protein hydrolysate, free amino acids, probiotics, LC-PUFA's and carbohydrates, such as lactose, saccharose, starch or maltodextrin.

DETAILED DESCRIPTION OF THE INVENTION

The present invention relates to the use of a beta-galactosidase (EC 3.2.1.23) derived from *C. terrestris* in the production of a hypoallergenic galacto-oligosaccharide (GOS) preparation, wherein said GOS preparation has a reduced capacity to induce an (IgE-mediated) allergic response in a subject, as compared to a GOS preparation obtained by transgalactosylation of lactose using a beta-galactosidase derived from *Bacillus circulans* or from *Aspergillus oryzae*.

It is to be noted that the organism "*Cryptococcus terrestris*" was recently renamed "*Papiliotrema terrestris*". The names "*Cryptococcus terrestris*" (*C. terrestris*) and "*Papiliotrema terrestris*" (*P. terrestris*) thus refer to the same organism. In the present description and in the claims, the name *Cryptococcus terrestris* is used throughout. However, the *Cryptococcus terrestris* organism can also be referred to by the name *Papiliotrema terrestris*. *Cryptococcus terrestris* is the basionym of *Papiliotrema terrestris* (Liu et al., *Towards an integrated phylogenetic classification of the Tremellomycetes*, Studies in Mycology 81, 85-147 (2016)).

As used herein, the term "hypoallergenic GOS preparation" (abbreviated to HA-GOS) refers to a GOS composition which, when administered to a subject suffering from at least one type of GOS-related allergy, i.e. an allergy caused by GOS produced by *Bacillus circulans* beta-galactosidase and/or by GOS produced by *Aspergillus oryzae* beta-galactosidase, evokes a reduced allergic response when compared to a GOS preparation produced by *Bacillus circulans* or *Aspergillus oryzae* beta-galactosidase.

In one aspect, the term "hypoallergenic GOS preparation" refers to a GOS preparation that evokes at least a reduced allergenicity in a subject suffering from *Bacillus circulans*-derived GOS-related allergy. In this aspect, a hypoallergenic GOS preparation evokes a reduced allergic response when compared to a GOS preparation produced by *Bacillus circulans*. More in particular, a hypoallergenic GOS preparation has a decreased score in a Skin Prick Test in the subject and/or in a Basophil Activation Test performed on a blood sample isolated from the subject when compared to a GOS preparation obtained by *Bacillus circulans*.

In another aspect, the term "hypoallergenic GOS preparation" refers to at least a reduced allergenicity in a subject suffering from *Aspergillus oryzae*-derived GOS-related allergy. In this aspect, a hypoallergenic GOS preparation evokes a reduced allergic response when compared to a GOS preparation produced by *Aspergillus oryzae*. More in particular, a hypoallergenic GOS preparation has a decreased score in a Skin Prick Test in the subject and/or in a Basophil Activation Test performed on a blood sample isolated from the subject when compared to a GOS preparation obtained by *Aspergillus oryzae*.

In one embodiment, the invention relates to the use of a beta-galactosidase (EC 3.2.1.23) derived from *C. terrestris* in the production of a hypoallergenic galacto-oligosaccharide (GOS) preparation, wherein said GOS preparation has a reduced capacity to induce an (IgE-mediated) allergic response in a subject, as compared to a GOS preparation obtained by transgalactosylation of lactose using a beta-galactosidase derived from *Bacillus circulans* or from *Aspergillus oryzae*.

In one embodiment, the invention relates to the use of a beta-galactosidase (EC 3.2.1.23) derived from *C. terrestris* in the production of a hypoallergenic galacto-oligosaccharide (GOS) preparation, wherein said GOS preparation has a reduced capacity to induce an (IgE-mediated) allergic response in a subject that is known to suffer from hypersensitivity to a GOS preparation obtained by transgalactosylation of lactose using *Bacillus circulans* or *Aspergillus oryzae*, as compared to a GOS preparation obtained by transgalactosylation of lactose using a beta-galactosidase derived from *Bacillus circulans* or from *Aspergillus oryzae*.

For example, the invention relates to the use of a beta-galactosidase (EC 3.2.1.23) derived from *C. terrestris* in the production of a hypoallergenic galacto-oligosaccharide (GOS) preparation, wherein said GOS preparation has a reduced capacity to induce an (IgE-mediated) allergic response in a subject that has an increased chance to suffer from hypersensitivity to a GOS preparation obtained by transgalactosylation of lactose using *Bacillus circulans* or *Aspergillus oryzae*, as compared to a GOS preparation obtained by transgalactosylation of lactose using a beta-galactosidase derived from *Bacillus circulans* or from *Aspergillus oryzae*.

In these embodiments, the subject is a mammal, in particular a human being. The subject may have any age. In a preferred embodiment, the subject is an adolescent or an adult. An adolescent is herein defined as a person having an age of from 13 to 20 years. An adult is herein defined as a person having an age of 20 years or higher. In another preferred embodiment, the subject is a child having an age of 3 years (36 months) to 13 years. In yet another preferred embodiment the subject is child having an age of 0 to 3 years, preferably having an age of 18 months or above, more preferably having an age of 24 months or above. The rare GOS-related allergy has not been reported in subjects having an age of 18 months or below. Therefore, in a preferred embodiment, the subject is an adult, an adolescent, or a child, having an age of 18 months or above, preferably having an age of 24 months or above, more preferably having an age of 36 months or above.

In view of the localized incidence of the 4'-GOS and/or 6'-GOS-related allergies in South East Asia (e.g. Singapore, Japan), the subject is preferably of South East Asian origin.

The β-galactosidase enzyme(s) for use in the present invention for the manufacture of hypoallergenic GOS are known per se from patent application PCT/JP2016/089001 by Amano. PCT/JP2016/089001 claims a priority date of Dec. 29, 2015, based on Japanese patent application no. 2015-257705.

PCT/JP2016/089001 discloses the screening of various kinds of microorganisms for β-galactosidase enzymes having desirable properties for industrial applications from viewpoints of heat resistance, pH stability, and others. This resulted in the finding of a microorganism (wild-type strain) of the genus *Cryptococcus*, in particular *Cryptococcus terrestris* (recently renamed *Papiliotrema terrestris*) which produces β-galactosidase that has a high optimum temperature and superior heat resistance, and in addition, excellent transgalactosylation activity. The *Cryptococcus terrestris*-derived beta-galactosidase described in PCT/JP2016/089001 are described in more detail below. PCT/JP2016/089001 also describes a method for producing oligosaccharides, comprising a step of subjecting the β-galactosidase enzyme to a reaction with a disaccharide, oligosaccharide, or polysaccharide having at least one of β-1,3-, β-1,4-, and β-1,6-linkages. Also disclosed is a method for producing oligosaccharides, comprising a step of subjecting the β-galactosidase enzyme to a reaction with lactose.

PCT/JP2016/089001 furthermore describes an oligosaccharide mixture obtained by the enzymes and methods disclosed therein, in particular an oligosaccharide mixture wherein 65% or more of the trisaccharides contained in the oligosaccharide mixture are composed of a linear oligosaccharide. It furthermore relates to the use of the β-galactosidase enzyme for the production of oligosaccharides, production of low-lactose milk, and productions of medicines or supplements for patients with lactose intolerance. PCT/JP2016/089001 specifically teaches that the GOS produced may be used as an intestinal *Bifidobacterium* growth factor.

Importantly however, PCT/JP2016/089001 does not address the allergenicity of the GOS mixture obtained using any of its enzymes. Hence, the present finding that GOS obtained by *Cryptococcus* enzymes according to PCT/JP2016/089001 has a surprisingly low allergenicity as compared to GOS prepared by *B. circulans* or by *A. oryzae* was not taught or suggested in the art.

The invention also relates to a hypoallergenic GOS preparation obtainable by transgalactosylation of lactose using a beta-galactosidase (EC 3.2.1.23) derived from *Cryptococcus terrestris* (recently renamed *Papiliotrema terrestris*), for use in preventing, at least partially, an (IgE-mediated) allergic response in a subject.

The present invention also provides a hypoallergenic GOS preparation obtainable by transgalactosylation of lactose using a beta-galactosidase (EC 3.2.1.23) derived from *Cryptococcus terrestris*, for use in preventing, at least partially, an (IgE-mediated) allergic response in a subject known to suffer or having an increased chance to suffer from hypersensitivity to a GOS preparation obtained by transgalactosylation of lactose using a beta-galactosidase derived from *Bacillus circulans* or from *Aspergillus oryzae*. In one embodiment, the subject is known to suffer, or has an increased chance to suffer, from hypersensitivity to a GOS preparation obtained by transgalactosylation of lactose using a beta-galactosidase derived from *Bacillus circulans*. In another embodiment, the subject is known to suffer, or has an increased chance to suffer, from hypersensitivity to a GOS preparation obtained by transgalactosylation of lactose using a beta-galactosidase derived from *Aspergillus oryzae*.

Also provided is a hypoallergenic GOS preparation obtainable by transgalactosylation of lactose using a beta-galactosidase (EC 3.2.1.23) derived from *C. terrestris*, for use in a nutritional composition for a subject known to suffer or having an increased chance to suffer from hypersensitivity to a GOS preparation obtained by transgalactosylation of lactose using *Bacillus circulans* or *Aspergillus oryzae* beta-galactosidase. In one embodiment, the subject is known to suffer, or has an increased chance to suffer, from hypersensitivity to a GOS preparation obtained by transgalactosylation of lactose using a beta-galactosidase derived from *Bacillus circulans*. In another embodiment, the subject is known to suffer, or has an increased chance to suffer, from hypersensitivity to a GOS preparation obtained by transgalactosylation of lactose using a beta-galactosidase derived from *Aspergillus oryzae*.

Also in these embodiments, the subject is a mammal, in particular a human being. The subject may have any age. In a preferred embodiment, the subject is an adolescent or an adult. In another preferred embodiment, the subject is a child having an age of 3 years (36 months) to 13 years. In yet another preferred embodiment the subject is child having an age of 0 to 3 years, preferably having an age of 18 months or above. In another preferred embodiment, the subject is an adult, an adolescent, or a child having an age of 18 months or above, preferably having an age of 24 months or above, more preferably having an age of 36 months or above. Also in these embodiments, the subject is preferably of South East Asian origin.

In another embodiment, the invention provides a method for at least partially preventing hypersensitivity to a GOS preparation in a subject, comprising administering a (preferably hypoallergenic) nutritional composition comprising a HA-GOS preparation obtainable by transgalactosylation of lactose using a beta-galactosidase (EC 3.2.1.23) derived from *C. terrestris* to the subject.

As used herein, a nutritional composition refers to any composition or formulation that goes into the alimentary canal for nutritional purposes, in whatever solid, liquid, gaseous state. Thus, a nutritional composition can be a food item or a drink item.

Also in this embodiment the subject is a mammal, in particular a human being, and may have any age. In a preferred embodiment, the subject is an adolescent or an adult. In another preferred embodiment, the subject is a child having an age of 3 years (36 months) to 13 years, preferably having an age of 18 months or above. In another preferred embodiment, the subject is an adult, an adolescent, or a child having an age of 18 months or above, preferably having an age of 24 months or above, more preferably having an age of 36 months or above. Also in these embodiments, the subject is preferably of South East Asian origin.

The invention also provides a nutritional composition comprising (i) a hypoallergenic GOS preparation obtainable by transgalactosylation of lactose using a beta-galactosidase (EC 3.2.1.23) derived from *C. terrestris* and (ii) at least one further ingredient selected from the group consisting of a hypoallergenic or non-allergenic protein source, preferably a non-allergenic milk protein hydrolysate, free amino acids, probiotics, a lipid source, and carbohydrates, such as lactose, saccharose, starch or maltodextrin.

Hypoallergenic or non-allergenic protein sources are known in the art, particularly for employment in infant formula. The terms non-allergenic hydrolysates and hydrolysates substantially free of allergenic proteins as used herein are interchangeable. They refer to protein hydrolysates that can be administered to infants having intolerance against dietary proteins, more particularly cow's milk proteins, without inducing allergic reactions. In one embodiment, the at least one further hypoallergenic or non-allergenic ingredient is selected from non-allergenic protein hydrolysates and hydrolysates substantially free of allergenic proteins, hypoallergenic protein sources, and hydrolyzed whey proteins. For example, U.S. Pat. No. 5,039,532 discloses a hydrolyzed whey protein material from which allergens consisting of alpha-lactalbumin, beta-lactoglobulin, serum albumin and immunoglobulins have not been removed and wherein the hydrolyzed protein material including hydrolyzed allergens is in a form of hydrolysis residues having a molecular weight not above 10,000 Da so that the hydrolyzed material is substantially free from allergenic proteins and allergens of protein origin. In one embodiment, a low-allergenic casein hydrolysate with peptides of maximally 3000 Da is included.

As a carbohydrate source, any type of carbohydrate, or a mixture of different carbohydrates, can serve which is normally used in children's food formulations. Suitable carbohydrate sources are disaccharides such as lactose and saccharose, monosaccharides, such as glucose, and maltodextrins, starch and carbohydrate sources having a prebiotic effect. In one embodiment, human milk oligosaccharides are used.

The lipid source in a composition according to the invention may be any type of lipid or combination of lipids which are suitable for use in (children's) nutritional products. Examples of suitable lipid sources are tri, di, and monoglycerides, phospholipids, sphingolipids, fatty acids, and esters or salts thereof. The lipids may have an animal, vegetable, microbial or synthetic origin. Of particular interest are polyunsaturated fatty acids (PUFAs) such as gamma linolenic acid (GLA), dihomo gamma linolenic acid (DHGLA), arachidonic acid (AA), stearidonic acid (SA), eicosapentaenoic acid (EPA), docosahexaenoic acid (DHA), docosapentaenoic acid (DPA) and conjugated linoleic acid (CLA). CLA is important in the protection against eczema and respiratory diseases in children. This particularly involves the cis-9, trans-11 and cis-12 isomers of CLA. Examples of suitable vegetable lipid sources include sun flower oil, high oleic sun flower oil, coconut oil, palm oil, palm kernel oil, soy bean oil, etc. Examples of suitable lipid sources of animal origin include milkfat, for example anhydrous milkfat (AMF), cream, etc. In a preferred embodiment, a combination of milkfat and lipids of vegetable origin are used.

In an embodiment, the composition according to the invention comprises a probiotic. In the context of the present invention, the term "probiotic" refers to a strain of probiotic bacteria. Probiotic bacteria are known in the art. Suitably, the probiotic bacteria are not genetically modified. Suitable probiotic bacteria include bacteria of the genus Bifidobacteria (e.g. *B. breve, B. longum, B. infantis, B. bifidum*), Lactobacillus (e.g. *L. Acidophilus, L. paracasei, L. johnsonii, L. plantarum, L. reuteri, L. rhamnosus, L. casei, L. lactis*), and Streptococcus (e.g. *S. thermophilus*). *B. breve* and *B. longum* are especially suitable probiotics. Suitable *B. breve* strains may for example be isolated from the faeces of healthy human milk-fed infants.

The combination of a prebiotic and a probiotic is also referred to as a "synbiotic". The probiotic may be present in the composition at any suitable concentration, suitably in a therapeutically effective amount or "amount effective for treating" in the context of the invention. Suitably, the probiotic is included in the present composition in an amount of 10 exp 2-10 exp 13 cfu per g dry weight of the composition, suitably 10 exp 5-10 exp 12 cfu/g, most suitably 10 exp 7-10 exp 10 cfu/g.

Further, the composition may contain one or more conventional micro ingredients, such as vitamins, antioxidants, minerals, free amino acids, nucleotides, taurine, carnitine and polyamines. Examples of suitable antioxidants are BHT, ascorbyl palmitate, vitamin E, alpha and beta carotene, lutein, zeaxanthin, lycopene and phospholipids.

Further provided is a method for providing a hypoallergenic nutritional composition, comprising (i) contacting a lactose feed with a beta-galactosidase (EC 3.2.1.23) derived from *C. terrestris* to provide a hypoallergenic galactooligosaccharide (GOS) preparation, and (ii) formulating said hypoallergenic GOS preparation together with at least one further hypoallergenic or non-allergenic ingredient into a hypoallergenic nutritional composition. Also provided is a hypoallergenic nutritional composition obtainable by a method of the invention.

The composition according to the invention can be used as a nutritional composition, nutritional therapy, nutritional support, as a medical food, as a food for special medical purposes or as a nutritional supplement. The present composition is suitably an enteral composition. The composition is administered to, or intended to be administered to, a subject in need thereof. The subject is a mammal, in particular a human being, and the subject may have any age. In a preferred embodiment, the subject is an adult. The subject may e.g. be an elderly person or a post-menopausal woman. The subject may also be a pregnant woman. Thus, in some embodiments, the present composition is a MUM composition for pregnant women. In another preferred embodiment, the subject is an adolescent.

In another preferred embodiment, the subject is a child having an age of 3 years (36 months) to 13 years. In this embodiment it is preferred that the child has an age of 3 years to 6 years. Thus, in some embodiments, the present composition is a growing-up milk for children having an age of 36 months or higher.

In yet another preferred embodiment the subject is child having an age of 0 to 3 years, preferably having an age of 18 months or above, more preferably having an age of 24 months or above. In this embodiment the subject is selected from the group consisting of children and infants, including toddlers, up to 3 years of age. Thus, in some embodiments, the present composition is an infant formula, a follow-on formula or a growing-up milk.

In a particular embodiment, the composition is for administration to subjects, in particular infants, at risk of developing allergy, especially cow's milk protein allergy (CMA). Infants that are known to be at risk of developing allergy include infants born from at least one parent who suffers from, or has suffered from, an atopic disorder (e.g. eczema) and/or an allergy, most in particular from CMA.

In view of the localized incidence of the 4'-GOS and/or 6'-GOS-related allergies in South East Asia (e.g. Singapore, Japan), the subject is preferably of South East Asian origin.

The enzyme for use according to the invention is a β-galactosidase derived from the yeast *Cryptococcus terrestris*. As described above, the organism *Cryptococcus terrestris* was recently renamed *Papiliotrema terrestris*, and the names "*Cryptococcus terrestris*" (*C. terrestris*) and "*Papiliotrema terrestris*" (*P. terrestris*) thus refer to the same organism. In the present description and in the claims, the name *Cryptococcus terrestris* is used throughout, but the *Cryptococcus terrestris* organism can also be referred to by the name *Papiliotrema terrestris*. Herein, by "β-galactosidase derived from *C. terrestris*" is meant a β-galactosidase enzyme produced by a microorganism (of either a wild-type strain or a mutant strain) which is classified into *Cryptococcus terrestris*, or a β-galactosidase enzyme obtained by genetic engineering procedures using the β-galactosidase gene from a microorganism (of either a wild-type strain or a mutant strain) which is classified into *Cryptococcus terrestris*. Therefore, the term "β-galactosidase derived from *Cryptococcus terrestris*" also encompasses a recombinant enzyme that is produced by a host microorganism into which the β-galactosidase gene (or a modified gene thereof) obtained from *Cryptococcus terrestris* has been introduced.

In general, a β-galactosidase shows a lactose hydrolyzing activity (an activity to hydrolyze lactose by the action on the β-1,4 bond) and a transgalactosylation activity (an activity to transfer galactose). Therefore, the expression "β-galactosidase activity" as used herein is intended to include such two activities.

As demonstrated in the Examples section, the inventors of PCT/JP2016/089001 were successful in isolating and purifying β-galactosidase enzymes having the above-described properties, from *Cryptococcus terrestris* strain MM13-F2171 and its mutant strains M2 and M6. Mutant strains (M2 and M6) were obtained from *Cryptococcus terrestris* strain MM13-F2171 by means of mutagenesis with UV treatment. *Cryptococcus terrestris* strains MM13-F2171 and M2 have been deposited at a depository, as described below, and are readily available.

<*Cryptococcus terrestris* Strain MM13-F2171>
  Depository: Patent Microorganisms Depositary, National Institute of Technology and Evaluation (Room 122, 2-5-8 Kazusa Kamatari, Kisarazu-shi, Chiba, 292-0818, JAPAN). Identification reference: *Cryptococcus terrestris* MM13-F2171. Date of deposit: Dec. 10, 2015. Accession number: NITE BP-02177;

<*Cryptococcus terrestris* Strain M2>
  Depository: Patent Microorganisms Depositary, National Institute of Technology and Evaluation (Room 122, 2-5-8 Kazusa Kamatari, Kisarazu-shi, Chiba, 292-0818, JAPAN). Identification reference: *Cryptococcus terrestris* APC-6431. Date of deposit: Dec. 10, 2015. Accession number: NITE BP-02178

Accordingly, in one embodiment the enzyme used in the present invention is derived from *Cryptococcus terrestris* strain MM13-F2171 (Accession Number: NITE BP-02177) or APC-6431 (Accession Number: NITE BP-02178).

The present invention thus also relates to the use of a beta-galactosidase (EC 3.2.1.23) derived from *Cryptococcus terrestris* in the production of a hypoallergenic galacto-oligosaccharide (GOS) preparation wherein said GOS preparation has a reduced capacity to induce an (IgE-mediated) allergic response in a subject, as compared to a GOS preparation obtained by transgalactosylation of lactose using a beta-galactosidase derived from *Bacillus circulans* or from *Aspergillus oryzae*, and wherein the beta-galactosidase is derived from *Cryptococcus terrestris* strain MM13-F2171 (Accession Number: NITE BP-02177) or APC-6431 (Accession Number: NITE BP-02178). Suitably, the subject is known to suffer or has an increased chance to suffer from hypersensitivity to a GOS preparation obtained by transgalactosylation of lactose using *Bacillus circulans* or *Aspergillus oryzae*. In one embodiment the subject is known to suffer or has an increased chance to suffer from hypersensitivity to a GOS preparation obtained by transgalactosylation of lactose using *Bacillus circulans* and said GOS preparation has a reduced capacity to induce an (IgE-mediated) allergic response in a subject, as compared to a GOS preparation obtained by transgalactosylation of lactose using a beta-galactosidase derived from *Bacillus circulans*. In another embodiment the subject is known to suffer or has an increased chance to suffer from hypersensitivity to a GOS preparation obtained by transgalactosylation of lactose using *Aspergillus oryzae* and said GOS preparation has a reduced capacity to induce an (IgE-mediated) allergic response in a subject, as compared to a GOS preparation obtained by transgalactosylation of lactose using a beta-galactosidase derived from *Aspergillus oryzae*.

The invention further relates to a hypoallergenic GOS preparation obtainable by transgalactosylation of lactose using a beta-galactosidase (EC 3.2.1.23) derived from *Cryptococcus terrestris*, for use in preventing, at least partially, an (IgE-mediated) allergic response in a subject, wherein the beta-galactosidase is derived from *Cryptococcus terrestris* strain MM13-F2171 (Accession Number: NITE BP-02177) or APC-6431 (Accession Number: NITE BP-02178). The invention further relates to a hypoallergenic GOS preparation obtainable by transgalactosylation of lactose using a beta-galactosidase (EC 3.2.1.23) derived from *Cryptococcus terrestris*, for use in preventing, at least partially, an (IgE-mediated) allergic response in a subject known to suffer or having an increased chance to suffer from hypersensitivity to a GOS preparation obtained by transgalactosylation of lactose using a beta-galactosidase derived from *Bacillus circulans* or from *Aspergillus oryzae*, wherein the beta-galactosidase is derived from *Cryptococcus terrestris* strain MM13-F2171 (Accession Number: NITE BP-02177) or APC-6431 (Accession Number: NITE BP-02178). In one embodiment the subject is known to suffer or has an increased chance to suffer from hypersensitivity to a GOS preparation obtained by transgalactosylation of lactose using a beta-galactosidase derived from *Bacillus circulans*. In another embodiment the subject is known to suffer or has an increased chance to suffer from hypersensitivity to a GOS preparation obtained by transgalactosylation of lactose using a beta-galactosidase derived from *Aspergillus oryzae*, Furthermore, the invention relates to a hypoallergenic GOS preparation obtainable by transgalactosylation of lactose using a beta-galactosidase (EC 3.2.1.23) derived from *Cryptococcus terrestris* for use in a nutritional composition for a subject known to suffer or having an increased chance to suffer from hypersensitivity to a GOS preparation obtained by transgalactosylation of lactose using *Bacillus circulans* or *Aspergillus oryzae*, wherein the beta-galactosidase is derived from *Cryptococcus terrestris* strain MM13-F2171 (Accession Number: NITE BP-02177) or APC-6431 (Accession Number: NITE BP-02178). In one embodiment, the subject is known to suffer or has an increased chance to suffer from hypersensitivity to a GOS preparation obtained by transgalactosylation of lactose using *Bacillus circulans*, In another embodiment, the subject is known to suffer or has an increased chance to suffer from hypersensitivity to a GOS preparation obtained by transgalactosylation of lactose using *Aspergillus oryzae*.

The invention also relates to a method for at least partially preventing hypersensitivity to a GOS preparation in a subject, comprising administering a (hypoallergenic) nutritional composition comprising a hypoallergenic GOS preparation obtainable by transgalactosylation of lactose using a beta-galactosidase (EC 3.2.1.23) derived from *Cryptococcus terrestris* to the subject, wherein the beta-galactosidase is derived from *Cryptococcus terrestris* strain MM13-F2171 (Accession Number: NITE BP-02177) or APC-6431 (Accession Number: NITE BP-02178).

Also in these embodiments, the subject is a mammal, in particular a human being. The subject may have any age. In a preferred embodiment, the subject is an adolescent or an adult. In another preferred embodiment, the subject is a child having an age of 3 to 13 years. In yet another preferred embodiment the subject is child having an age of 0 to 3 years, preferably having an age of 18 months or above. In another preferred embodiment, the subject is an adult, an adolescent, or a child having an age of 18 months or above, preferably having an age of 24 months or above. Also in these embodiments, the subject is preferably of South East Asian origin.

Furthermore, PCT/JP2016/089001 describes three kinds of β-galactosidase produced by mutant strains derived from the *Cryptococcus* microorganism (mutant strain enzymes 1, 2, and 3), and determined their amino acid sequences. These three β-galactosidase enzymes were found to have a partial sequence of the full-length amino acid sequence of the wild-type strain enzyme (the wild-type strain enzyme is shown in FIG. 1A; SEQ ID NO: 1), which is deduced from its gene sequence. Specifically, these mutant enzymes are one having an amino acid sequence in which the N-terminal 130 amino acid residues of the full-length amino acid sequence of the wild-type strain enzyme are deleted, which is referred to as "mutant strain enzyme 1" for the purpose of description (see FIG. 1B; SEQ ID NO: 2); one having an amino acid sequence in which the N-terminal 136 amino acid residues of the full-length amino acid sequence of the wild-type strain enzyme are deleted (see FIG. 1C; SEQ ID NO:3), which is referred to as "mutant strain enzyme 2" for the purpose of description; and one having an amino acid sequence in which the N-terminal 141 amino acid residues of the full-length amino acid sequence of the wild-type strain enzyme are deleted (see FIG. 1D; SEQ ID NO:4), which is referred to as "mutant strain enzyme 3".

Accordingly, a β-galactosidase enzyme derived from *C. terrestris* for use in a preferred embodiment of the present invention comprises the amino acid sequence of any one of SEQ ID NOs: 1, 2, 3 or 4, or an amino acid sequence equivalent to said amino acid sequence.

Also, a combination of two or more β-galactosidase enzymes derived from *C. terrestris* may be used, wherein each enzyme comprises an amino acid sequence of any one of SEQ ID NOs: 1, 2, 3 or 4 or an amino acid sequence equivalent to any one of said amino acid sequences. In one embodiment, at least one mutant enzyme (SEQ ID NO's 2, 3 or 4, or an equivalent thereof) is used. Preferably two or more mutant enzymes are used, optionally in combination with the wild type enzyme. For example, a combination of two or more enzymes, each enzyme comprising an amino acid sequence of SEQ ID NO: 2, SEQ ID NO: 3 and SEQ ID NO: 4, or an amino acid sequence equivalent to said amino acid sequences, is used. In a specific aspect, the enzyme combination comprises the three distinct mutant enzymes and the wildtype enzyme.

The term "equivalent amino acid sequence" in this case means an amino acid sequence which is partially different from the reference amino acid sequence (i.e. amino acid sequence of any one of SEQ ID NOs: 1 to 4), but the difference does not substantially influence the function of the protein (beta-galactosidase activity). Thus, an enzyme having a polypeptide chain of the equivalent amino acid sequence shows a beta-galactosidase activity.

The degree of the activity is not particularly limited as long as the function of a beta-galactosidase can be exhibited, but is preferably equivalent to or higher than that of the enzyme having a polypeptide chain of the reference sequence. Preferably, the length of the equivalent amino acid sequence is not longer than that of the sequence of SEQ ID NO: 1.

The term "partial difference in the amino acid sequence" typically means mutation (change) in the amino acid sequence caused by deletion or substitution of one to several (up to, for example, 3, 5, 7, or 10) amino acids composing the amino acid sequence, or addition, insertion, or a combination thereof of one to several (up to, for example, 3, 5, 7, or 10) amino acids. The difference in the amino acid sequence is acceptable as long as the beta-galactosidase activity is maintained (the activity may be varied to a degree). As long as the conditions are satisfied, the position of the difference in the amino acid sequence is not particularly limited, and the difference may arise in a plurality of positions. The term "plurality" means, for example, a number corresponding to less than about 20%, preferably less than about 15%, more preferably less than about 10%, even more preferably less than about 5% of the total amino acids, and most preferably less than about 1%. More specifically, the equivalent protein has, for example, about 80% or more, preferably about 85% or more, more preferably about 90% or more, much more preferably about 95% or more, even more preferably about 97% or more, and most preferably about 99% or more identity with the reference amino acid sequence.

The difference of the amino acid sequence may arise in a plurality of positions. Preferably, the equivalence protein is obtained by causing conservative amino acid substitution in an amino acid residue which is not essential for beta-galactosidase activity. The term "conservative amino acid substitution" means the substitution of an amino acid residue with another amino acid residue having a side chain with similar properties.

Amino acid residues are classified into several families according to their side chains, such as basic side chains (for example, lysine, arginine, and histidine), acidic side chains (for example, aspartic acid and glutamic acid), uncharged polar side chains (for example, glycine, asparagine, glutamine, serine, threonine, tyrosine, and cysteine), nonpolar side chains (for example, alanine, valine, leucine, isoleucine, proline, phenylalanine, methionine, and tryptophan), β-branched side chains (for example, threonine, valine, and isoleucine), and aromatic side chains (for example, tyrosine, phenylalanine, tryptophan, and histidine). Conservative amino acid substitution is preferably the substitution between amino acid residues in one family.

The identity (%) between two amino acid sequences or two nucleic acid sequences (hereinafter, the term "two sequences" are used for representing either of two sequences) can be determined by the following procedure. Firstly, two sequences are aligned for optimum comparison of the two sequences (for example, a gap may be introduced into the first sequence so as to optimize the alignment with respect to the second sequence). When a molecule (amino acid residue or nucleotide) at a specific position in the first sequence and a molecule in the corresponding position in the second sequence are the same as each other, the molecules in the positions are defined as being identical. The identity between two sequences is a function of the number of identical positions shared by the two sequences (i.e., identity (%)=number of identical positions/total number of positions %100). Preferably, the number and size of the gaps, which are required to optimize the alignment of the two sequences, are taken into consideration.

The comparison and determination of the identity between two sequences can be carried out by using a mathematical algorithm. A specific example of the mathematical algorithm that can be used for comparing the sequences includes an algorithm described in Karlin and Altschul (1990) Proc. Natl. Acad. Sci. USA 87:2264-68 and modified by Karlin and Altschul (1993) Proc. Natl. Acad. Sci. USA 90:5873-77. However, the algorithm is not necessarily limited to this. Such an algorithm is incorporated in NBLAST program and XBLAST program (version 2.0) described in Altschul et al. (1990) J. Mol. Biol. 215: 403-10. In order to obtain an equivalent nucleic acid sequence, for example, BLAST nucleotide search with score=100 and word length=12 may be carried out by the NBLAST program. In order to obtain an equivalent amino acid sequence, for example, BLAST polypeptide search with score=50 and word length=3 may be carried out by the XBLAST program. In order to obtain gapped alignments for comparison, Gapped BLAST described in Altschul et al., (1997) Amino Acids Research 25(17): 3389-3402 can be utilized. In using BLAST and Gapped BLAST, the default parameters of the corresponding programs (e.g.,)(BLAST and NBLAST) can be used. Another example of the mathematical algorithm that can be used for comparing sequences includes an algorithm described in Meyers and Miller (1988) Comput. Appl. Biosci. 4: 11-17. Such programs are incorporated into the ALIGN program that can be used for, for example, GENESTREAM network server (IGH Montpellier, France) or ISREC server. When the ALIGN program is used for comparison of the amino acid sequences, for example, PAM120 weight residue table can be used in which a gap length penalty is 12 and a gap penalty is 4.

The identity between two amino acid sequences can be determined by using the GAP program in the GCG software package, using Blossom 62 matrix or PAM250 matrix with the gap weight of 12, 10, 8, 6, or 4, and the gap length weight of 2, 3, or 4. The identity between two nucleic acid sequences can be determined by using the GAP program in the GCG software package, with the gap weight of 50, and the gap length weight of 3. The enzyme may be a portion of a larger protein (for example, a fusion protein). Examples of the sequence added to a fused protein include the sequences/tags useful for purification of multiple histidine residues, and addition sequences which ensures stability in recombinant production.

The present invention also relates to the use of a beta-galactosidase (EC 3.2.1.23) in the production of a hypoallergenic galacto-oligosaccharide (GOS) preparation, wherein said GOS preparation has a reduced capacity to induce an (IgE-mediated) allergic response in a subject as compared to a GOS preparation obtained by transgalactosylation of lactose using a beta-galactosidase derived from *Bacillus circulans* or from *Aspergillus oryzae*, and wherein the beta-galactosidase comprises an amino acid sequence according to any of SEQ ID NO: 1, 2, 3 or 4, or an amino acid sequence that is at least 80%, preferably at least 85%, more preferably at least 90%, even more preferably at least 95%, yet even more preferably at least 97%, and most preferably at least 99% identical to any of SEQ ID NO: 1, 2, 3 or 4.

The present invention also relates to the use of a beta-galactosidase (EC 3.2.1.23) derived from *Cryptococcus terrestris* in the production of a hypoallergenic galacto-oligosaccharide (GOS) preparation, wherein said GOS preparation has a reduced capacity to induce an (IgE-mediated) allergic response in a subject as compared to a GOS preparation obtained by transgalactosylation of lactose using a beta-galactosidase derived from *Bacillus circulans* or from *Aspergillus oryzae*, and wherein the beta-galactosidase comprises an amino acid sequence according to any of SEQ ID NO: 1, 2, 3 or 4, or an amino acid sequence that is at least 80%, preferably at least 85%, more preferably at least 90%, even more preferably at least 95%, yet even more preferably at least 97%, and most preferably at least 99% identical to any of SEQ ID NO: 1, 2, 3 or 4. Suitably, the subject is known to suffer or has an increased chance to suffer from hypersensitivity to a GOS preparation obtained by transgalactosylation of lactose using *Bacillus circulans* or *Aspergillus oryzae*. In one embodiment the subject is known to suffer or has an increased chance to suffer from hypersensitivity to a GOS preparation obtained by transgalactosylation of lactose using *Bacillus circulans* and said GOS preparation has a reduced capacity to induce an (IgE-mediated) allergic response in a subject, as compared to a GOS preparation obtained by transgalactosylation of lactose using a beta-galactosidase derived from *Bacillus circulans*. In another embodiment the subject is known to suffer or has an increased chance to suffer from hypersensitivity to a GOS preparation obtained by transgalactosylation of lactose using *Aspergillus oryzae* and said GOS preparation has a reduced capacity to induce an (IgE-mediated) allergic response in a subject, as compared to a GOS preparation obtained by transgalactosylation of lactose using a beta-galactosidase derived from *Aspergillus oryzae*. The invention further relates to a hypoallergenic GOS preparation obtainable by transgalactosylation of lactose using a beta-galactosidase (EC 3.2.1.23), for use in preventing, at least partially, an (IgE-mediated) allergic response in a subject, wherein the beta-galactosidase comprises an amino acid sequence according to any of SEQ ID NO: 1, 2, 3 or 4, or an amino acid sequence that is at least 80%, preferably at least 85%, more preferably at least 90%, even more preferably at least 95%, yet even more preferably at least 97%, and most preferably at least 99% identical to any of SEQ ID NO: 1, 2, 3 or 4. In a further embodiment, said subject is known to suffer from or has an increased chance to suffer from hypersensitivity to a GOS preparation obtained by transgalactosylation of lactose using a beta-galactosidase derived from *Bacillus circulans* or from *Aspergillus oryzae*. The invention further relates to a hypoallergenic GOS preparation obtainable by transgalactosylation of lactose using a beta-galactosidase (EC 3.2.1.23) derived from *Cryptococcus terrestris*, for use in preventing, at least partially, an (IgE-mediated) allergic response in a subject known to suffer or having an increased chance to suffer from hypersensitivity to a GOS preparation obtained by transgalactosylation of lactose using a beta-galactosidase derived from *Bacillus circulans* or from *Aspergillus oryzae*, wherein the beta-galactosidase comprises an amino acid sequence according to any of SEQ ID NO: 1, 2, 3 or 4, or an amino acid sequence that is at least 80%, preferably at least 85%, more preferably at least 90%, even more preferably at least 95%, yet even more preferably at least 97%, and most preferably at least 99% identical to any of SEQ ID NO: 1, 2, 3 or 4. In one embodiment the subject is known to suffer or has an increased chance to suffer from hypersensitivity to a GOS preparation obtained by transgalactosylation of lactose using a beta-galactosidase derived from *Bacillus circulans*. In another embodiment the subject is known to suffer or has an increased chance to suffer from hypersensitivity to a GOS preparation obtained by transgalactosylation of lactose using a beta-galactosidase derived from *Aspergillus oryzae*, Furthermore, the invention relates to a hypoallergenic GOS preparation obtainable by transgalactosylation of lactose using a beta-galactosidase (EC 3.2.1.23) derived from *Cryptococcus terrestris* for use in a nutritional composition for a subject known to suffer or having an increased chance to suffer from hypersensitivity to a GOS preparation obtained by transgalactosylation of lactose using *Bacillus circulans* or *Aspergillus oryzae*, wherein the beta-galactosidase comprises an amino acid sequence according to any of SEQ ID NO: 1, 2, 3 or 4, or an amino acid sequence that is at least 80%, preferably at least 85%, more preferably at least 90%, even more preferably at least 95%, yet even more preferably at least 97%, and most preferably at least 99% identical to any of SEQ ID NO: 1, 2, 3 or 4. In one embodiment, the subject is known to suffer or has an increased chance to suffer from hypersensitivity to a GOS preparation obtained by transgalactosylation of lactose using *Bacillus circulans*, In another embodiment, the subject is known to suffer or has an increased chance to suffer from hypersensitivity to a GOS preparation obtained by transgalactosylation of lactose using *Aspergillus oryzae*.

The invention also relates to a method for at least partially preventing hypersensitivity to a GOS preparation in a subject, comprising administering a (hypoallergenic) nutritional composition comprising a hypoallergenic GOS preparation obtainable by transgalactosylation of lactose using a beta-galactosidase (EC 3.2.1.23) derived from *Cryptococcus terrestris* to the subject, wherein the beta-galactosidase comprises an amino acid sequence according to any of SEQ ID NO: 1, 2, 3 or 4, or an amino acid sequence that is at least 80%, preferably at least 85%, more preferably at least 90%, even more preferably at least 95%, yet even more preferably at least 99%, and most preferably at least 98% identical to any of SEQ ID NO: 1, 2, 3 or 4.

Also in these embodiments, the subject is a mammal, in particular a human being. The subject may have any age. In a preferred embodiment, the subject is an adolescent or an adult. In another preferred embodiment, the subject is a child having an age of 3 to 13 years. In yet another preferred embodiment the subject is child having an age of 0 to 3 years, preferably having an age of 18 months or above. In another preferred embodiment, the subject is an adult, an adolescent, or a child having an age of 18 months or above, preferably having an age of 24 months or above. Also in these embodiments, the subject is preferably of South East Asian origin.

An enzyme for use in the present invention having the above-described amino acid sequence may also be prepared by a genetic engineering technique. For example, an appropriate host cell (for example, *Escherichia coli*) is transformed by a DNA encoding the present enzyme, and the protein expressed in the transformant is collected, and thereby preparing the present enzyme. The collected protein is treated as appropriate according to the intended use. The enzyme thus obtained as a recombinant protein may be subjected to various modifications. For example, a protein composed of a recombinant protein linked to any peptide or protein can be obtained by producing a recombinant protein using a vector into which a DNA encoding the enzyme has been inserted together with other appropriate DNA. In addition, modification for causing addition of a sugar chain and/or a lipid, or N- or C-terminal processing may be carried out. These modifications allow, for example, extraction of a recombinant protein, simplification of purification, or addition of biological functions.

The inventors of PCT/JP2016/089001 also characterized the enzymatic properties of the novel β-galactosidase enzymes that had been obtained. Thus, the enzyme for use in the present invention may be characterized by enzymatic properties described below in (1) to (3), as described in PCT/JP2016/089001.

(1) Enzymatic Action

The enzyme has a lactose hydrolyzing activity and a transgalactosylation activity, wherein the activity of the enzyme to transfer a galactosyl residue via β-1,4-linkage is superior to that via β-1,6-, β-1,3-, or β-1,2-linkage. That is, the enzyme has excellent activity to transfer a galactosyl residue via β-1,4-linkage. Therefore, the use of the enzyme allows an efficient production of a (hypoallergenic) product having the transferred sugar residue attached via β-1,4-linkage. For example, reaction of the enzyme with lactose, which is a substrate for the enzyme, generates a mixture of trisaccharide oligosaccharides that is rich in linear oligosaccharides. In cases of trisaccharide oligosaccharides obtained when lactose is used as a substrate for reaction with the present enzyme under reaction conditions described in the Examples section of PCT/JP2016/089001 (in the subsection titled "Examination on oligosaccharide production ability 1"), 65% or more, preferably 70% or more, further preferably 72% or more, still further preferably 73% or more, more preferably 75% or more, of the resulting trisaccharide oligosaccharides are composed of oligosaccharides with mere β-1,4-glycosidic linkages (O-β-D-galactopyranosyl-(1→4)-O-β-D-galactopyranosyl-(1→4)-D-glucose).

In these cases, the linear oligosaccharide produced by the enzyme is a galacto-oligosaccharide. In general, the galacto-oligosaccharide is represented by Gal-(Gal)n-Glc, wherein n is 1 to 5 or so, Gal is a galactose residue and Glc is a glucose residue. The type of linkage between sugar residues includes β-1,4, β-1,6, β-1,3, and β-1,2, and besides these, α-1,3, α-1,6, and others.

Therefore, a "galacto-oligosaccharide (GOS)" as used herein means a galacto-oligosaccharide of two or more sugar residues, i.e., having a degree of polymerization of 2 or more, excluding lactose.

(2) Optimum Temperature

The enzyme has an optimum temperature of 70° C. Such a high optimum temperature of the enzyme is advantageous for use as an enzyme for the production of oligosaccharides. When the enzyme is used for the production of oligosaccharides, the process (reaction) temperature can be set to be higher. Herein, the optimum temperature can be determined by a method in which measurements are made using acetate buffer (pH 6.0) and with lactose as a substrate.

(3) Molecular Weight

The wild-type strain enzyme and mutant strain enzymes 1 to 3 disclosed in PCT/JP2016/089001 each comprise a sugar chain(s); when the molecular weights of these enzymes were determined by SDS-PAGE after removal of N- and O-linked sugar chains, they were found to have a molecular weight of 104 kDa (for the wild-type strain enzyme), 64 kDa (for mutant strain enzyme 1), 61 kDa (for mutant strain enzyme 2), and 61 kDa (for mutant strain enzyme 3). On the basis of these findings, according to one embodiment, the enzyme without sugar chains for use in the present invention has a molecular weight of 104 kDa (by SDS-PAGE). According to another embodiment, the enzyme without sugar chains that is used in the present invention has a molecular weight of 64 kDa (by SDS-PAGE). According to further another embodiment, the enzyme without sugar chains has a molecular weight of 61 kDa (by SDS-PAGE). The above-mentioned enzymes when not subjected to treatments for removing sugar chains
were found to have a molecular weight of 120 kDa (for the wild-type strain enzyme), 71 kDa (for mutant strain enzyme 1), 66 kDa (for mutant strain enzyme 2), and 66 kDa (for mutant strain enzyme 3).

The enzyme for use according to the present invention may be further characterized by enzymatic properties described below in (4) to (6).

(4) Optimum pH

The enzyme has an optimum pH of 4 to 5. The optimum pH is determined, for example, on the basis of the results from measurements made using 0.1 M glycine buffer in the pH range of pH 2 to 3, 0.1 M citrate buffer in the pH range of pH 3 to 6, 0.1 M acetate buffer in the pH range of pH 5 to 6, 0.1 M phosphate buffer in the pH range of pH 7 to 8, and 0.1 M sodium carbonate buffer in the pH range of pH 9 to 10.

(5) pH Stability

In one embodiment, the present enzyme exhibits stable enzymatic activity in the pH range of pH 2 to 8, and in another embodiment, in the pH range of pH 2 to 9. In other words, if the pH of an enzyme solution to be subjected to treatments is within this pH range, then the enzyme after pH treatments at 40° C. for 30 minutes shows an activity of 80% or more of the maximal activity. The pH stability is determined, for example, on the basis of the results from measurements made using 0.1 M glycine buffer in the pH range of pH 2 to 3, 0.1 M citrate buffer in the pH range of pH 3 to 6,
0.1 M acetate buffer in the pH range of pH 5 to 6, 0.1 M phosphate buffer in the pH range of pH 7 to 8, and 0.1 M sodium carbonate buffer in the pH range of pH 9 to 10.

(6) Thermostability

In one embodiment, the enzyme for use as herein disclosed retains an activity of 80% or more of the maximal activity, even when the enzyme is treated for 30 minutes in acetate buffer (pH 6.0) under temperature conditions of 30° C. to 60° C. In another embodiment, the enzyme retains an activity of 80% or more of the activity, even when the enzyme is treated for 30 minutes in acetate buffer (pH 6.0) under temperature conditions of 30° C. to 65° C.

PCT/JP2016/089001 also discloses genes encoding an enzyme for use in the present invention. In one embodiment, the gene includes a DNA that encodes an amino acid sequence of any one of SEQ ID NOs: 1 to 4. Specific examples of the embodiment are the cDNA consisting of the nucleic acid sequence of SEQ ID NO: 5 (encoding the amino acid sequence of SEQ ID NO: 1), the cDNA consisting of the nucleic acid sequence of SEQ ID NO: 6 (encoding the amino acid sequence of SEQ ID NO: 2), the cDNA consisting of the nucleic acid sequence of SEQ ID NO: 7 (encoding the amino acid sequence of SEQ ID NO: 3), and the cDNA consisting of the nucleic acid sequence of SEQ ID NO: 8 (encoding the amino acid sequence of SEQ ID NO: 4). A further example is the genome DNA consisting of SEQ ID NO: 16. This genome DNA corresponds to the cDNA of SEQ ID NO: 5.

The gene is typically used in preparation of the beta-galactosidase enzymes derived from C. terrestris disclosed in PCT/JP2016/089001 and used in the present invention. According to a genetic engineering procedure using the gene encoding the enzyme, the enzyme can be obtained in a more homogeneous state. Further, the method can be a preferable method also in the case of preparing a large amount of the enzyme. Degeneracy of a codon is also considered.

As disclosed in PCT/JP2016/089001, the gene for use in the preparation of the beta-galactosidase enzymes derived from C. terrestris can be prepared in an isolated state by using a standard genetic engineering technique, a molecular biological technique, a biochemical technique, a chemical synthesis, a PCR method (e.g. an overlap extension PCR) or a combination thereof, with reference to sequence information disclosed in the attached sequence listing.

In general, and as also described in PCT/JP2016/089001, when a part of DNA encoding a certain protein is modified, a protein encoded by the modified DNA may sometimes have the equal function to that of a protein encoded by the DNA before modification. That is to say, the modification of the DNA sequence does not have a substantial effect on the function of the encoded protein, so that the function of the encoded protein may be maintained before and after the modification. Therefore the DNA encoding a protein may having a nucleic acid sequence equivalent to the reference base sequence (i.e., any one of SEQ ID NO: 5 to 8, 16) and having the β-galactosidase activity (hereinafter also referred to as "equivalent DNA").

The "equivalent nucleic acid sequence" herein denotes a nucleic acid sequence which is partly different from the reference nucleic acid sequence but in which the function (herein, β-galactosidase activity) of the protein encoded by the sequence is not substantially affected by the difference.

A specific example of the equivalent DNA includes DNA that hybridizes to the complementary base sequence of the reference nucleic acid sequence under stringent conditions. Herein, the "stringent conditions" are referred to as conditions in which a so-called specific hybrid is formed but a nonspecific hybrid is not formed. Such stringent conditions are known to persons skilled in the art. Such stringent conditions can be set with reference to, for example, Molecular Cloning (Third Edition, Cold Spring Harbor Laboratory Press, New York) and Current protocols in molecular biology (edited by Frederick M. Ausubel et al., 1987). An example of the stringent conditions can include a condition in which a hybridization solution (50% formamide, 10×SSC (0.15 M NaCl, 15 mM sodium citrate, pH 7.0), 5×Denhardt solution, 1% SDS, 10% dextran sulfate, 10 µg/ml denatured salmon sperm DNA, and 50 mM phosphate buffer (pH 7.5)) is used and incubated at about 42° C. to about 50° C., thereafter, washed with 0.1×SSC and 0.1% SDS at about 65° C. to about 70° C. Further preferable stringent conditions can include, for example, a condition in which a hybridization solution (50% formamide, 5×SSC (0.15 M NaCl, 15 mM sodium citrate, pH 7.0), 1×Denhardt solution, 1% SDS, 10% dextran sulfate, 10 µg/ml denatured salmon sperm DNA, and 50 mM phosphate buffer (pH 7.5)) is used.

As disclosed in PCT/JP2016/089001, another specific example of the equivalent DNA can include DNA encoding a protein having a nucleic acid sequence which includes substitution, deletion, insertion, addition or inversion in one or a plurality of nucleic acids (preferably one to several nucleic acids) in the reference sequence, and which has a β-galactosidase activity. The substitution, deletion, or the like, of the nucleic acid may occur in a plurality of sites. The "plurality" herein denotes, for example, 2 to 40 bases, preferably 2 to 20 nucleic acids, and more preferably 2 to 10 nucleic acids, although it depends upon the positions or types of the amino acid residue in the three-dimensional structure of the protein encoded by the DNA. The equivalent DNA shows a 60% or more identity for example, preferably a 70% or more identity, more preferably a 80% or more identity, more and more preferably a 85% or more identity, much more preferably a 90% or more identity, even more preferably 95% or more identity, and most preferably a 99% or more identity with the reference nucleic acid sequence. The above-mentioned equivalent DNA can be obtained by modifying the reference DNA so as to include substitution, deletion, insertion, addition and/or inversion of nucleic acid by using treatment with a restriction enzyme; treatment with exonuclease, DNA ligase, etc; introduction of mutation by a site-directed mutagenesis (Molecular Cloning, Third Edition, Chapter 13, Cold Spring Harbor Laboratory Press, New York) and random mutagenesis (Molecular Cloning, Third Edition, Chapter 13, Cold Spring Harbor Laboratory Press, New York), and the like. Furthermore, the equivalent DNA can be also obtained by other methods such as irradiation with ultraviolet ray. A further example of the equivalent DNA can include DNA having difference in nucleic acid as mentioned above due to polymorphism represented by SNP (single nucleotide polymorphism).

Therefore the nucleic acid may also be a nucleic acid having a complementary base sequence to the base sequence of the gene encoding the enzymes used in the present invention. For example, the nucleic acid may have a base sequence with an identity of at least about 60%, 70%, 80%, 85%, 90%, 95%, 98%, 99%, or 99.9% to the base sequence of the gene encoding the enzymes used in the present invention, or the complementary base sequence thereto. The DNA may also be a recombinant DNA containing the gene encoding the enzymes used in the present invention.

The recombinant DNA is suitably provided in, for example, a form of a vector. The term "vector" in the present specification refers to a nucleic acid molecule that can transfer a nucleic acid inserted in the vector to a target such as a cell. A suitable vector is selected according to its intended use (cloning, expression of a protein) and in consideration of a kind of a host cell.

Examples include a M13 phage or an altered form thereof, a λ phage or an altered form thereof, and pBR322 or an altered form thereof (e.g., pB325, pAT153, pUC8), etc. as a vector having *Escherichia coli* as a host, pYepSec1, pMFa, and pYES2 as a vector having a yeast as a host, pAc, pVL, etc. as a vector having an insect cell as a host, and pCDM8, pMT2PC, etc. as a vector having a mammal cell as a host. The vector is preferably an expression vector. The "expression vector" refers to a vector capable of introducing a nucleic acid inserted in the expression vector into a target cell (host cell) and expressing it in the cell. The expression vector generally contains a promoter sequence necessary for expression of a nucleic acid inserted, an enhancer sequence for promoting expression, and the like.

An expression vector containing a selective marker can also be used. When such an expression vector is used, presence or absence (and its degree) of introduction of the expression vector can be confirmed using a selective marker.

Insertion of DNA into the vector, insertion of a selective marker gene (if necessary), insertion of a promoter (if necessary), and the like can be performed by using a standard recombinant DNA technique (for example, a known method of using a restriction enzyme and a DNA ligase, which can be referred in Molecular Cloning, Third Edition, 1.84, Cold Spring Harbor Laboratory Press, New York).

As described in PCT/JP2016/089001, an enzyme for use in the present invention is advantageously produced by a transformant into which the recombinant DNA encoding the beta-galactosidase (EC 3.2.1.23) derived from *C. terrestris* is introduced, such that the gene exists as an exogenous molecule. Preferably, the transformant is prepared by transfection or transformation using the vector mentioned above. The transfection and transformation can be carried out using methods known in the art, for example, by a calcium phosphate co-precipitation method, electroporation, lipofection, microinjection, a method by Hanahan (Hanahan, D., J. Mol. Biol. 166, 557-580 (1983)), a lithium acetate method (Schiestl, R. H. et al., Curr. Genet. 16, 339-346 (1989)), protoplast-polyethylene glycol method (Yelton, M. M. et al., Proc Natl. Acad. Sci. 81, 1470-1474 (1984)), and the like.

The host cell is not particularly limited as long as the present enzyme can be expressed, and it can be selected from, for example, *Bacillus* genus bacteria (e.g. *Bacillus subtilis, Bacillus licheniformis, Bacillus circulans*, etc.), lactic acid bacteria (e.g. *Lactococcus, Lactobacillus, Streptococcus, Leuconostoc, Bifidobacterium*, etc.), other bacteria (e.g. *Escherichia, Streptomyces*, etc.), yeast (e.g. *Saccharomyces, Kluyveromyces, Candida, Torula, Torulopsis, Pichia, Schizosaccharomyces*, etc.), and filamentous fungi (Eumycetes) (e.g. *Aspergillus* genus fungi such as *Aspergillus oryzae* and *Aspergillus niger, Penicillium* genus fungi, *Trichoderma* genus fungi, *Fusarium* genus fungi, etc.).

PCT/JP2016/089001 also describes a method for producing a β-galactosidase enzyme which is advantageously used in the present invention. Disclosed is a method comprising the steps of culturing cells of *Cryptococcus terrestris* (step (1)); and a step of collecting the β-galactosidase enzyme from the cultured medium and/or cells (step (2)). Preferably, as the *Cryptococcus terrestris*, use is made of *Cryptococcus terrestris* strain MM13-F2171 or a mutant strain thereof, for example, *Cryptococcus terrestris* APC-6431 (strain M2) and further mutant strains thereof.

Conditions and methods for culturing cells of *Cryptococcus terrestris* are not particularly limited, as long as the enzyme is produced. Thus, methods and culture conditions that are suitable for culturing a microorganism to be used can be set as appropriate, with the proviso that the enzyme is produced. The cell culture may comprise mixtures of two or more *Cryptococcus terrestris* strains, for example wild-type strain MM13-F2171 and one or more mutant strains thereof, for example, *Cryptococcus terrestris* APC-6431 (strain M2) and/or *Cryptococcus terrestris* strain M6. In these cases, two or more enzymes can be isolated and purified simultaneously.

Although the culturing may be by either liquid culture or solid culture, liquid culture is preferably employed. As the medium, any medium can be used as long as microorganisms to be used can grow. For example, a medium supplemented with a carbon source such as glucose, sucrose, gentiobiose, soluble starch, glycerin, dextrin, molasses, and organic acid; and further, a nitrogen source such as ammonium sulfate, ammonium carbonate, ammonium phosphate, ammonium acetate, or peptone, yeast extract, corn steep liquor, casein hydrolysate, bran, and meat extract; and furthermore, an inorganic salt such as potassium salt, magnesium salt, sodium salt, phosphate salt, manganese salt, iron salt, and zinc salt, and the like, can be used.

In order to promote the growth of transformants to be used, vitamin, amino acid, and the like, may be added to the medium. The medium may be cultured under the aerobic conditions such that the pH of the medium is adjusted to, for example, about 3 to 8 (preferably about 4 to 7), and the culture temperature is generally about 20° C. to 40° C. (preferably about 25° C. to 35° C.) for 1 to 10 days (preferably 3 to 6 days). An example of the culture method may include a shake culture method, and an aerobic submerged culture method by using a jar fermenter.

After culturing under the above conditions, the target protein(s) is collected from the culture solution or the cell bodies (step (2)). When it is collected from the culture solution, the enzyme can be obtained by separation and purification by removing insoluble matters by, for example, filtration of culture supernatant, centrifugation, and the like, followed by carrying out, for example, concentration by ultrafiltration membrane, salting out by ammonium sulfate precipitation, dialysis, various types of chromatography of an ion-exchange resin or an appropriate combination thereof. On the other hand, when it is collected from cell bodies, the target protein(s) can be obtained by pulverizing the cell bodies by pressuring treatment, ultrasonic treatment, or the like, followed by separation and purification thereof similar to the above.

After collection of the cell bodies from a culture solution by filtration, centrifugation, etc., a series of processes (pulverizing, separation, and purification of cell bodies) mentioned above may be carried out. The β-galactosidase(s) for use in the present invention may also be produced by using the above-mentioned transformant. The transformant is then cultured under conditions such that a protein encoded by a gene introduced therein is produced (step (i)).

The culture conditions of transformant are known as to various vector-host systems, and a person skilled in the art can easily set an appropriate culture condition. Following the culturing step, the produced protein (β-galactosidase) is collected (step (ii)). Collection and subsequent purification can be conducted in the same manner as the above embodiment. The purification degree of β-galactosidase(s) is not particularly limited. Furthermore, the final form of the β-galactosidase(s) may be a liquid state or a solid state (including a powder form).

The purified enzyme(s) can be provided in a powder form, for example, by freeze drying, vacuum drying, or spray drying. For example, the purified enzyme(s) may be previously dissolved in a phosphoric acid buffer solution, a triethanol amine buffer solution, a tris-hydrochloric acid buffer solution, or a GOOD buffer solution. Preferably, a phosphoric acid buffer solution and a triethanol amine buffer solution can be used. Note that, for the GOOD buffer solution herein, PIPES, MES or MOPS is exemplified.

BRIEF DESCRIPTION OF THE DRAWINGS

FIGS. 1a-1i: amino acid sequences of exemplary beta-galactosidase (EC 3.2.1.23) enzymes derived from *Cryptococcus terrestris*. A) SEQ ID NO: 1: wild-type enzyme; B) SEQ ID NO: 2: mutant strain enzyme 1; C) SEQ ID NO: 3: mutant strain enzyme 2; D) SEQ ID NO: 4: mutant strain enzyme 3.

EXPERIMENTAL SECTION

β-Galactosidase Derived from *C. terrestris*

Figure 2A:
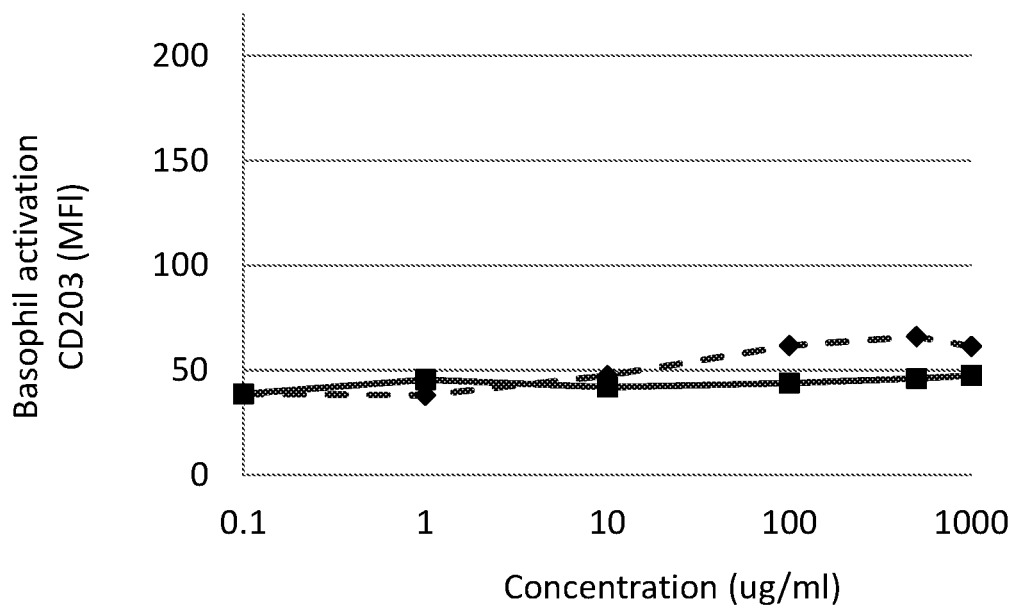
FIGS. 2a and 2b: Basophil activation in test subject #1 as measured by expression of the basophil activation marker CD203c (FIG. 2a, MFI=Mean Fluorescence) and percentage of cells expressing the basophil activation marker CD63 (FIG. 2b). Squares represent HA-GOS (solid line in the graph). Diamonds represent REF-GOS (dotted line in the graph). For details see Example 2.

The beta-galactosidase enzymes derived from *C. terrestris* as used in the present invention were obtained from Amano Enzyme Inc. (Nagoya, Japan). These beta-galactosidase enzymes and methods for their preparation are disclosed in PCT/JP2016/089001 by Amano. The method for the preparation of beta-galactosidase enzymes derived from *C. terrestris*, as well as the enzyme properties, as disclosed in PCT/JP2016/089001 are described below in paragraphs 1 to 8.

1. Obtaining a Wild-Type Beta-Galactosidase from *C. terrestris*

In order to obtain a β-galactosidase enzyme suitable for the production of galacto-oligosaccharides, various kinds of microorganisms were screened. As a result, it turned out that a microorganism of *Cryptococcus terrestris* contained in a soil sample that had been collected near Heho Airport in Myanmar in October 2013 was a promising producer strain for β-galactosidase. An attempt was made to purify β-galactosidase from this microbial strain (*Cryptococcus terrestris* strain MM13-F2171). *Cryptococcus terrestris* strain MM13-F2171 was deposited on Dec. 10, 2015 at the Patent Microorganisms Depositary, National Institute of Technology and Evaluation, under the name of *Cryptococcus terrestris* MM13-F2171, to which the Accession Number NITE BP-02177 was assigned.

*Cryptococcus terrestris* strain MM13-F2171 was cultured in a liquid medium (2.0% lactose, 2.0% Yeast Extract, 0.1% $KH_2PO_4$, 0.05% $MgSO_4 \cdot 7H_2O$, pH 5.0) at 30° C. for 4 days with shaking (at 200 revolutions per minute). After the culturing was completed, about 3 L supernatant was collected by centrifugation, and then subjected to concentration and desalting treatment with an ultra-filtration membrane (AIP-1013D with a membrane inner size of 0.8 mm; Asahi Kasei Chemicals Corp.). In the desalting treatment, 20 mM acetate buffer (pH 6.0) was used.

The concentrated solution was loaded onto an anion-exchange column HiTrap DEAE FF (GE Healthcare Biosciences), which had been equilibrated with 20 mM acetate buffer (pH 6.0). Absorbed fractions were eluted with a gradient using 20 mM acetate buffer (pH 6.0) containing 1 M NaCl, and measured for enzyme activity. Fractions with enzyme activity were pooled, and then subjected to dialysis against 20 mM acetate buffer (pH 6.0) containing 1.8 M ammonium sulfate. The enzyme-active fraction obtained after the dialysis was loaded onto a hydrophobic column HiTrap Phenyl HP (GE Healthcare Biosciences), which had been equilibrated with 20 mM acetate buffer (pH 6.0) containing 1.8 M ammonium sulfate. Absorbed fractions were eluted with a gradient using 20 mM acetate buffer (pH 6.0), and measured for enzyme activity. Fractions with enzyme activity were pooled, and then subjected to dialysis against 20 mM acetate buffer (pH 6.0) containing 0.2 M NaCl.

The enzyme-active fraction obtained after the dialysis was loaded onto a gel filtration column HiLoad Superdex 200 prep grade (GE Healthcare Biosciences), which had been equilibrated with 20 mM acetate buffer (pH 6.0) containing 0.2 M NaCl, and then fractions with enzyme activity were collected. The enzyme had a molecular weight of about 266 kDa when determined by a gel filtration method using this HiLoad Superdex 200 prep grade column.

When this result is considered in combination with the results of SDS-PAGE analysis (see below), it is supposed that the enzyme is in the form of a dimer.

Subsequently, the molecular weight of the purified wild-type strain enzyme was determined by SDS-PAGE. First, samples of the purified wild-type strain enzyme were subjected to denaturation (in a denaturing buffer in a boiling water bath for 10 minutes), followed by treatments for removal of O-linked sugar chains (using both O-glycosidase and neuraminidase; O-Glycosidase & Neuraminidase Bundle, New England Biolabs) and/or N-linked sugar chains (using PNGase F; New England Biolabs). The conditions for these enzyme treatments followed the protocols provided with the respective enzymes. After the treatments, the molecular weights of the resulting products were determined by SDS-PAGE.

The wild-type strain enzyme was found to have a molecular weight of 120 kDa after no treatment, 106 kDa after removal of O-linked sugar chains, 104 kDa after removal of N-linked sugar chains, and 104 kDa after removal of both O-linked and N-linked sugar chains.

2. Internal Amino Acid Sequences of the Purified Enzyme

Analysis of the internal amino acid sequence of the purified enzyme revealed that the enzyme comprises the following internal amino acid sequences:

```
                                    (SEQ ID NO: 9)
           GVQYVDYNSPT (SEQ ID NO: 10)
           FLFGWATAAQQ
                                    (SEQ ID NO: 11)
           QAYQIGIFAEPIYNT (SEQ ID NO: 12)
           PSIWDWAS,
           and
                                    (SEQ ID NO: 13)
           EEPPFAYVPE.
```

3. Determination of the Gene Sequence of the Wild-Type Strain Enzyme

An attempt was made to determine the gene sequence encoding the β-galactosidase produced by *Cryptococcus terrestris* strain MM13-F2171. *Cryptococcus terrestris* strain MM13-F2171 was cultured in a liquid medium (2.0% lactose, 2.0% Yeast Extract, 0.1% $KH_2PO_4$, 0.05% $MgSO_4 \cdot 7H_2O$, pH 5.0) at 30° C. for 24 hours with shaking (at 200 revolutions per minute). After the culturing was completed, cells were harvested. Total RNA was prepared in accordance with the protocol of the RNeasy Mini Kit (QIAGEN) for RNA extract ion from yeast cells (mechanical disruption of cells). The synthesis of cDNAs from the resulting total RNA was performed using the SMARTer RACE 5'/3' kit (TaKaRa), and then 5' and 3' RACE PCR react ions were carried out. The 5'RACE GSP primer used had the sequence GATTACGCCAAGCTTgcaaagatccc-gatctggtacgcctg (SEQ ID NO: 14), and the 3'RACE GSP primer used had the sequence GATTACGC-CAAGCTTttcctgtttggctgggcgaccgcc (SEQ ID NO: 15). The base sequences of the resulting RACE PCR products were analyzed to determine the full-length cDNA sequence (SEQ ID NO: 5). The putative amino acid sequence encoded by the full-length cDNA sequence is of SEQ ID NO: 1.

By further investigation, the genomic DNA sequence encoding the β-galactosidase produced by *Cryptococcus terrestris* strain MM13-F2171 (SEQ ID NO: 16) was successfully determined.

4. Properties of the Purified Wild-Type Enzyme (1) Optimum pH and pH Stability

The optimum pH and pH stability of the purified wild-type enzyme were examined using a lactose hydrolyzing activity as an indicator. Examinations for optimum pH were performed using 0.1 M glycine buffer in the pH range of pH 2 to 3, 0.1 M citrate buffer in the pH range of pH 3 to 6, 0.1 M acetate buffer in the pH range of pH 5 to 6, 0.1 M phosphate buffer in the pH range of pH 7 to 8, and 0.1 M sodium carbonate buffer in the pH range of pH 9 to 10. The results from enzyme activity measurements at different pHs showed that the purified enzyme has an optimum pH of 4 to 5.

The pH stability of the purified enzyme was examined by heating it at 40° C. for 30 minutes in buffers of different pHs (using the above-described buffers) and then measuring the residual enzyme activity. The results from residual enzyme activity measurements at different pHs showed that the purified enzyme exhibited stable enzyme activity in the pH range of pH 2 to 8.

(2) Optimum Temperature and Thermostability

To examine the optimum temperature of the purified enzyme, acetate buffer (pH 6.0) was used and the lactose hydrolyzing activity was measured at different temperatures. The results from enzyme activity measurements at different temperatures showed that the purified enzyme was found to have an optimum temperature of 70° C. To examine the thermostability of the purified enzyme, the lactose hydrolyzing activity was measured after the enzyme was heated in acetate buffer (pH 6.0) for 30 minutes at different temperatures. The results from enzyme activity measurements at different temperatures showed that the purified enzyme was stable between 30° C. and 60° C. and the enzyme activity was retained at levels of 80% or more of the activity.

5. Examination of Oligosaccharide Production Ability of Wild-Type Enzyme (1) Methods The purified enzyme was examined for the ability to produce oligosaccharides. One unit (1 U) of the purified wild-type strain enzyme per 1 g of lactose was added to aliquots of a 53% lactose solution that had been preheated to specified reaction temperatures, which then were subjected to reaction at those temperatures for 24 hours. The reaction solutions after the reaction was completed were analyzed by HPLC (under the conditions described below) to determine the composition of sugars contained therein. The results from determination of the composition of sugars allow an evaluation of the transglycosylation activity.

Examinations were made for the degrees of polymerization of galacto-oligosaccharides (GOSs) and of branching of trisaccharides when the production of galacto-oligosaccharides by the purified enzyme (wild-type strain enzyme) reached a yield of about 50%. Reactions were carried out in accordance with the above-described procedures, and at 65° C. for 24 hours as conditions where the production of GOSs by the purified enzyme (derived from *Cryptococcus terrestris*) reached a yield of about 50%.

The degree of polymerization was determined by using an MCI™ GEL CK04S column (Mitsubishi Chemical Corporation); H$_2$O as eluent; 0.4 ml/min flow rate; RI detector; 80° C. column temperature.

The degree of branching was determined by using a Shodex column (registered trademark) Asahipak NH2P-40 3E (Showa Denko K.K.); MeCN:H$_2$O=75:25 (vol:vol) as eluent; 0.35 ml/min flow rate; RI detector; 25° C. column temperature.

(2) Results

Measurements results were used to calculate the content (%) of galacto-oligosaccharides (GOSs) in the total amount of sugars (total sugar), contained in the respective reaction solutions and the proportions (%) of respective GOSs with the indicated degrees of polymerization, at the indicated reaction temperatures. Results are shown in Table 1. The purified enzyme (wild-type strain enzyme) was found to have excellent GOS-producing ability. In addition, the wild-type strain enzyme was found to exhibit high levels of transglycosylation activity under high temperature conditions.

TABLE 1

GOS production with wild-type β-galactosidase at varying temperatures.

| Enzyme | Reaction temperature | Amount of GOS | Ratio in GOS (%) | | |
|---|---|---|---|---|---|
| | | | ≥ DP4 | DP3 | DP2* |
| WT strain enzyme | 65° C. | 53.4 | 22.1 | 51.8 | 26.1 |
| | 70° C. | 54.2 | 25.8 | 47.4 | 26.8 |

*Lactose not included

Measurements results were used to calculate the proportions (%) of respective GOSs with the indicated degrees of polymerization. Typical results for the degrees of polymerization of GOSs when the purified enzyme (wild-type strain enzyme) was used are shown in Table 2. The wild-type strain enzyme (*Cryptococcus terrestris* derived enzyme) was found to have excellent GOS-producing ability and to efficiently produce oligosaccharides, particularly trisaccharides and higher saccharides.

TABLE 2

Comparison of GOS production with various enzymes.

| Strain (enzyme) | Ratio in GOS (%) | | |
|---|---|---|---|
| | ≥ DP4 | DP3 | DP2* |
| *Cryptococcus laurentii* | 18.0 | 55.8 | 26.1 |
| *Sporobolomyces singularis* | 13.5 | 54.5 | 32.0 |
| *C. terrestris* MM13-F2171 (WT strain enzyme) | 16.7 | 57.5 | 25.8 |

*Lactose not included

Measurements results were used to calculate the proportions (%) of linear and branched oligosaccharide in the resultant trisaccharides and to compare the ratios of trisaccharides with branched chain (i.e. the degrees of branching of trisaccharides) between the enzymes derived from *Cryptococcus terrestris* and known other β-galactosidase-producing strains. The results for the degrees of branching of GOSs when the purified enzyme (wild-type strain enzyme) was used are shown in Table 3. The wild-type strain enzyme (*Cryptococcus terrestris* derived enzyme) was found to produce predominantly linear oligosaccharides. Thus, it was revealed that the wild-type strain enzyme has transglycosylation activity in which the sugar chain is specifically transferred via β-1,4-glycosidic linkage and in particular, is less capable of transglycosylating so as to form β-1,6-glycosidic linkage.

TABLE 3

Comparison of Degree of branching of DP3 GOS produced with various enzymes.

| Strain (enzyme) | Ratio in DP3 (%) | | |
|---|---|---|---|
| | β1-4 | β1-6 | β1-2, β1-3 |
| *Cryptococcus laurentii* | 71.9 | 12.0 | 16.1 |
| *Sporobolomyces singularis* | 70.1 | 5.7 | 24.3 |
| *C. terrestris* MM13-F2171 (WT strain enzyme) | 76.3 | 1.5 | 22.1 |

6. Obtaining β-Galactosidase Enzymes Produced by Mutant Strains, and Determination of Amino Acid Sequences and Molecular Weights Thereof Two mutant strains (M2 and M6) were obtained from *Cryptococcus terrestris* strain MM13-F2171 by means of mutagenesis with UV treatment. β-Galactosidase enzymes produced by these mutant strains were purified in procedures similar to those described above for the wild-type enzyme. Strains M2 and M6 each were found to have a high ability to produce mutant strain enzymes 1 to 3; strain M2 was observed to have a particularly high ability to produce mutant strain enzyme 1, and strain M6 to produce mutant strain enzymes 2 and 3. *Cryptococcus terrestris* strain M2 was deposited at Dec. 10, 2015 at the Patent Microorganisms Depositary, National Institute of Technology and Evaluation, under the name of *Cryptococcus terrestris* APC-6431, to which the Accession Number NITE BP-02178 was assigned.

The amino acid sequences of the obtained purified enzymes, i.e., one enzyme derived from mutant strain M2 (mutant strain enzyme 1) and two enzymes derived from mutant strain M6 (mutant strain enzymes 2 and 3), were determined. First, N-terminal amino acid sequences of mutant strain enzymes 1 to 3 were determined using a protein sequencer (PPSQ-31A, SHIMADZU CORPORATION). Then, the cDNA sequence of the wild-type strain enzyme (SEQ ID NO: 5) was searched for the base sequence corresponding to the N-terminal amino acid sequence of each of the mutant strain enzymes, thereby to determine the cDNA sequence encoding each of the mutant strain enzymes. The amino acid sequence of mutant strain enzyme 1 (SEQ ID NO: 2) corresponds to one having a deletion of the N-terminal 130 amino acid residues of the full-length amino acid sequence of the wild-type strain enzyme (SEQ ID NO: 1), which is deduced from the cDNA sequence encoding the wild-type strain enzyme (SEQ ID NO: 5). Similarly, the amino acid sequence of mutant strain enzyme 2 (SEQ ID NO: 3) corresponds to one having a deletion of the N-terminal 136 amino acid residues of the full-length amino acid sequence of the wild-type strain enzyme (SEQ ID NO: 1), while the amino acid sequence of mutant strain enzyme 3 (SEQ ID NO: 4) corresponds to one having a deletion of the N-terminal 141 amino acid residues of the full-length amino acid sequence of the wild-type strain enzyme (SEQ ID NO: 1).

Subsequently, the molecular weights of these mutant strain enzymes were determined by SDS-PAGE. Procedures and conditions for removing sugar chains were in accordance with those described above for the wild-type enzyme. The molecular weights of the respective mutant strain enzymes were determined when the enzymes were subjected to no treatment, and treatments for removal of N-linked sugar chains, O-linked sugar chains, and both N-linked and O-linked sugar chains. On the basis of the results of SDS-PAGE analysis, it was observed that strain M2 produces mutant strain enzymes 2 and 3, in addition to mutant strain enzyme 1.

The mutant strain enzyme 1 was found to have a molecular weight of 71 kDa after no treatment, 65 kDa after removal of O-linked sugar chains, 64 kDa after removal of N-linked sugar chains, and 64 kDa after removal of both O-linked and N-linked sugar chains.

The mutant strain enzyme 2 was found to have a molecular weight of 66 kDa after no treatment, 63 kDa after removal of O-linked sugar chains, 61 kDa after removal of N-linked sugar chains, and 61 kDa after removal of both O-linked and N-linked sugar chains.

The mutant strain enzyme 3 was found to have a molecular weight of 66 kDa after no treatment, 62 kDa after removal of O-linked sugar chains, 61 kDa after removal of N-linked sugar chains, and 61 kDa after removal of both O-linked and N-linked sugar chains.

7. Examination of Oligosaccharide Production Ability of Mutant Strain Enzymes 1, 2 and 3

(1) Methods

To aliquots of a lactose solution was added the purified enzyme derived from strain M2 (mutant strain enzyme 1) or M6 (mutant strain enzyme 3), and the mixtures were subjected to reaction. Examinations were performed for the degrees of polymerization and branching of sugars contained in the reaction solutions after the reaction was completed. The reaction conditions and measurements of the degrees of polymerization and branching were in accordance with those described above under 5.

(2) Results

Measurements results were used to calculate the content (%) of GOSs in the total amount of the sugars (total sugar) contained in the respective reaction solutions and the proportions (%) of respective GOSs with the indicated degrees of polymerization, at the indicated reaction temperatures (Table 4). The purified enzyme (mutant strain enzyme) was found to have excellent GOS-producing ability. In addition, the mutant strain enzyme was found to exhibit high levels of sugar transfer activity under high temperature conditions. It can also be found that there were no differences in GOS producing ability between the wild-type stain enzyme and the mutant strain enzyme.

TABLE 4

GOS production with mutant strain enzyme 3 at varying temperatures.

| Enzyme | Reaction temperature | Amount of GOS | Ratio in GOS (%) | | |
| --- | --- | --- | --- | --- | --- |
| | | | ≥ DP4 | DP3 | DP2* |
| C. terrestris M6 (mutant strain enzyme 3) | 50° C. | 46.9 | 6.4 | 68.9 | 24.7 |
| | 60° C. | 52.1 | 16.1 | 58.2 | 25.8 |
| | 65° C. | 53.2 | 20.9 | 53.4 | 26.0 |
| | 70° C. | 53.9 | 24.5 | 49.2 | 26.3 |

*Lactose not included

Measurements results were used to calculate the proportions (%) of respective GOSs with the indicated degrees of polymerization. Typical results for the degrees of polymerization of GOSs when the purified mutated enzymes derived from strains M2 (mutant strain enzyme 1) and M6 (mutant strain enzyme 3) were used are shown in Table 5. The mutant strain enzymes were found to have excellent GOS-producing ability and to efficiently produce oligosaccharides, particularly trisaccharides and higher saccharides. It can also be found that there were no differences in GOS producing ability between the wild-type stain enzyme and the mutant strain enzymes.

TABLE 5

Comparison of GOS production with various enzymes.

| Strain (enzyme) | Ratio in GOS (%) | | |
| --- | --- | --- | --- |
| | ≥ DP4 | DP3 | DP2* |
| Cryptococcus laurentii | 18.0 | 55.8 | 26.1 |
| Sporobolomyces singularis | 13.5 | 54.5 | 32.0 |
| C. terrestris M2 (mutant strain enzyme 1) | 14.2 | 60.5 | 25.3 |
| C. terrestris M6 (mutant strain enzyme 3) | 19.9 | 54.2 | 25.8 |

*Lactose not included

Measurements results were used to calculate the proportions (%) of linear and branched oligosaccharide in the resultant trisaccharides and to compare the ratios of trisaccharides with branched chain (i.e. the degrees of branching of trisaccharides) between the wild-type strain enzymes and two mutant strain enzymes Table 6.

TABLE 6

Comparison of Degree of branching of DP3 GOS produced with various enzymes.

| Strain (enzyme) | Ratio in DP3 (%) | | |
| --- | --- | --- | --- |
| | β1-4 | β1-6 | β1-2, β1-3 |
| Cryptococcus laurentii | 71.9 | 12.0 | 16.1 |
| Sporobolomyces singularis | 70.1 | 5.7 | 24.3 |
| C. terrestris M2 (mutant strain enzyme 1) | 79.0 | 0.4 | 20.7 |
| C. terrestris M6 (mutant strain enzyme 3) | 75.2 | 2.7 | 22.1 |

The mutant strain enzymes (mutated, *Cryptococcus terrestris* derived enzymes) were found to produce predominantly linear oligosaccharides. Thus, it was revealed that the mutant strain enzymes have transglycosylation activity in which the sugar chain is specifically transferred via β-1,4-glycosidic linkage and in particular, is less capable of transglycosylating so as to form β-1,6-glycosidic linkage. It was also observed that the wild-type strain enzyme and the mutant strain enzymes have a comparable ability to produce GOSs and do not have any substantial differences in terms of properties as β-galactosidase. Mutant strain enzyme 2 is a β-galactosidase enzyme of which the amino acid sequence is shorter by six amino acid residues at the N terminus than that of mutant strain enzyme 1 and longer by five amino acid residues at the N-terminus than that of mutant strain enzyme 3. Since it is apparent from the above results that an amino acid sequence in an N-terminal region does not affect enzymatic properties, it can be inferred that mutant strain enzyme 2 also have enzymatic properties equivalent to those of mutant strain enzymes 1 and 3.

8. Properties of Mutant Strain Enzymes 1 and 3

The purified, mutated enzymes (see the above section described under 6) were used to examine properties of mutant strain enzymes 1 and 3. The experimental methods were similar to those described for the wild-type strain enzyme (see the above section described under 4).

(1) Optimum pH and pH Stability

Mutant strain enzymes 1 and 3 each were found to have an optimum pH of 4 to 5. Mutant strain enzymes 1 and 3 each were found to exhibit stable activity in the pH range of pH 2 to 9.

(2) Optimum Temperature and Thermostability

Mutant strain enzymes 1 and 3 each were found to have an optimum temperature of 70° C. Mutant strain enzymes 1 and 3 each were found to be stable between 30° C. and 65° C. and to retain enzyme activity at levels of 80% or more of the activity.

Example 1: Preparation of Hypoallergenic GOS (HA-GOS)

Synthesis of GOS Preparation

Four batches of a GOS preparation (referred to as PT 731-741-631-431) were produced by the transgalactosylation of lactose by four batches of *Cryptococcus terrestris* β-galactosidase enzyme (obtained from Amano Enzyme Inc., batch numbers GFEO0450731SDR, GFEO0450741SDR, GFEN1052631SDR and GFEO0750431SDR). For each batch, a lactose slurry (~50% (w/w) Lactopure, batch no. 502392; MFG:13-07-2014) was used as substrate. This lactose slurry was heated to 95° C. to dissolve the lactose. Subsequently the lactose solution was cooled down to the reaction temperature of 65° C. A very mild citrate buffer (2-3 mM) was added in order to adjust and stabilize the pH. Per gram lactose, 0.94 LU enzyme was used. During the reaction the pH was adjusted by citric acid and sodium hydroxide when needed. 42 Hours after the enzyme addition, the reaction was stopped by heating 30 min. at 90° C.

TABLE 7

Proximate analysis of the various batches of HA-GOS

| Test Parameter | HA-GOS PT731 | HA-GOS PT741 | HA-GOS PT631 | HA-GOS PT431 | REF-GOS* (ref |
|---|---|---|---|---|---|
| Dry matter (%) | 76.08 | 75.09 | 76.39 | 76.79 | 74.26 |
| Galacto-oligosaccharides (% on dry matter) | 62.2 | 63.14 | 63.8 | 64.82 | 58.14 |
| Nitrogen (% on dry matter) | 0.0016 | <0.0016 | <0.0016 | <0.0016 | 0.0016 |
| Protein (% on dry matter) | 0.01 | <0.01 | <0.01 | <0.01 | 0.01 |
| Sulphated ash (% on dry matter) | <0.01 | 0.02 | 0.02 | 0.02 | 0.1 |
| Lactose (% on dry matter) | 18.3 | 17.6 | 16.62 | 17.07 | 20.04 |
| Glucose (% on dry matter) | 18.4 | 18.16 | 18.39 | 17.24 | 20.36 |
| Galactose (% on dry matter) | 1.03 | 1.1 | 1.19 | 0.88 | 1.46 |
| Nitrite | 0.08 | 0.07 | 0.07 | 0.07 | 0.02 |
| pH | 3.34 | 3.24 | 3.08 | 3.2 | 2.9 |

*Conventional GOS prepared by transgalactosylation of lactose under the action of *B. circulans*.

GOS Degree of Polymerisation (DP) analysis was performed according to established methods. Table 8 shows that the results of the Degree of Polymerization analysis of hypoallergenic GOS (HA-GOS) of the present invention are highly similar to those found in the reference GOS preparation obtained using the enzyme from *B. circulans* (REF-GOS).

TABLE 8

Analytical results for DP-analysis

| HA-GOS | Galactose | Glucose | DP2 | DP3 | DP4 | DP5 | DP6 | DP7 | Total |
|---|---|---|---|---|---|---|---|---|---|
| PT731 | 0.91 | 18.93 | 41.15 | 26.02 | 11.30 | 1.56 | 0.14 | — | 100 |
| PT741 | 1.19 | 18.68 | 41.21 | 25.99 | 11.26 | 1.53 | 0.14 | — | 100 |
| PT631 | 1.13 | 19.11 | 40.59 | 25.63 | 11.67 | 1.71 | 0.16 | — | 100 |
| PT431 | 0.82 | 18.08 | 41.25 | 26.43 | 11.67 | 1.60 | 0.15 | — | 100 |
| REF-GOS | 1.31 | 21.12 | 37.42 | 22.02 | 10.76 | 4.88 | 1.90 | 0.60 | 100 |

Down Stream Processing

After the enzyme reaction was terminated by heating, the solution was run on an Ion Exchange column (cation exchange followed by anion exchange)), followed by reduction of the pH to 3.2 using citric acid. After pasteurization at 75° C. the GOS was concentrated to approximately 75% dry matter.

The analyses of the thus obtained batches of GOS preparation are indicated in Table 7. In this table it is shown that the specifications of the four batches produced by applying four batches of *P. terrestris* β-Galactosidase enzyme are highly consistent (low inter-batch variation). Differences with REF-GOS, which is prepared by transgalactosylation of lactose under the action of *B. circulans*, are very small.

Example 2: Oral Challenge Test

This example describes a double-blind placebo-controlled oral challenge test to demonstrate the reduced allergenicity of HA-GOS in in multiple human subjects with known galacto-oligosaccharide allergy. In addition, a skin prick test and basophil activation test were performed with HA-GOS.

Materials

HA-GOS (batch PT731; see Example 1) and a commercial GOS preparation obtained using *B. circulans* enzyme (REF-GOS) were included in the tests. The materials were stored at room temperature in the dark until use.

Subjects

Eligible subjects were selected from the cohort previously studied for the prevalence of GOS-allergy in a Singapore atopic population, as described in the paper by Soh et al., 2015[10]. Seven eligible subjects were approached for participation in the study. Two subjects refused to participate. Therefore, five adult subjects with confirmed GOS-related allergy were recalled to the clinic for a skin prick test, blood sample drawing and twice for a double-blind placebo-controlled oral challenge test with HA-GOS (minimum time between challenges was 2 weeks). The study was approved by the hospital's institutional ethical review board (IRB protocol "Testing hypoallergenicity of a modified galacto-oligosaccharide in patients with known galacto-oligosaccharide allergy". Written consent of all subjects was obtained prior to the start of the study.

Skin Prick Test, Basophil Activation Test and Oral Challenge Test

Skin prick testing to HA-GOS was carried out by the clinical research coordinator on the middle of the back or the forearm. Histamine and REF-GOS were used as positive controls. The wheal size for each sample was recorded and used as the degree of skin test reactivity.

A Basophil Activation Test was performed on patient blood samples. Heparinized peripheral blood aliquots (100 μL) were pre-incubated at 37° C. for 5 minutes and then incubated with 100 μL of PBS (negative control), anti-IgE antibody (positive control, G7-18; BD Biosciences, San Jose, Calif.) or diluted GOS samples for 15 minutes (37° C.). After incubation, cells were washed in PBS-EDTA (20 mmol/L) and then incubated with phycoerythrin-labeled anti-human IgE (Ige21; eBioscience, San Jose, Calif.), biotin-labeled anti-human CD203c (NP4D6; BioLegend, San Jose, Calif.), and fluorescein isothiocyanate-labeled anti-human CD63 (MEM-259, BioLegend) mAbs for 20 minutes at 48° C. Expression of CD203c and CD63 are both markers for basophil activation. After washing the cells with 1% BSA/PBS, allophycocyanin-conjugated streptavidin (BD Biosciences) was added and incubated for 15 minutes at 48° C. Thereafter, samples were subjected to erythrocyte lysis with 2 mL of FACS Lysing Solution (BD Biosciences). Cells were then washed, resuspended in 1% BSA/PBS, and analysed by means of FACSCalibur (BD Biosciences). Basophils were detected on the basis of side-scatter characteristics and expression of IgE (IgEhigh)[7].

An Oral Food Challenge Test was performed by administration of escalating dosages of HA-GOS at 30 minute intervals to achieve a total cumulative dose of 4 grams (see Table 9 below). The total dose of 4 grams was chosen, as this was the maximum dose that triggered a clinical reaction in 5 patients who had anaphylaxis to REF-GOS, as reported by Chiang et al.[7]. A solution of 0.8 g GOS/100 ml water was used in the study and prepared fresh on the day of the challenge.

TABLE 9

Dose regimen of the oral food challenge test

| Time | Proportion of GOS mixture to meal size | Amount of GOS in grams | Amount of GOS in ml | Cumulative dose in grams |
|---|---|---|---|---|
| 0' | 5% | 0.10 | 12.5 | 0.10 |
| 30' | 25% | 0.50 | 62.5 | 0.60 |
| 60' | 70% | 1.4 | 175 | 2.00 |
| 90' | 100% | 2.00 | 250 | 4.00 |

As placebo, we used a mixture of glucose, lactose and citric acid to mimic the non-oligosaccharide composition and taste of HA-GOS. Preparation of the test solution for the oral challenges was done by laboratory personnel not involved in the actual oral challenge testing. Furthermore, the preparation of the solution was checked by a second person to avoid any mix up. The physician performing the oral challenge test was blinded for the test material (HA-GOS or Placebo solution).

Results

Results Skin Prick Test and Oral Challenge Test

Seven subjects with prior proven REF-GOS-related allergy were eligible for an oral challenge with HA-GOS. These subjects had had reactions typical of an acute allergic reaction within 30 minutes of the threshold dose during challenge with REF-GOS. All had positive skin prick tests to REF-GOS.

Eventually, four subjects were challenged with HA-GOS and placebo in the current study (subject #1, #2, #4 and #5). Prior to the HA-GOS challenge, all were skin prick test negative to HA-GOS.

The detailed results of the oral challenge (OC) and skin prick test (SPT) with HA-GOS are presented in the table below. The response to a REF-GOS challenge (performed roughly two-and-a-half years before the current challenge with HA-GOS) is also described in table 10, for reference.

TABLE 10

Results of the oral challenge (OC) and skin prick test (SPT) with HA-GOS

| Subject number (male/female) | Allergy background | REF-GOS OC (date) | REF-GOS OC response | SPT REF-GOS (wheal) | SPT HA-GOS (wheal) | HA-GOS OC (date) | HA-GOS OC response |
|---|---|---|---|---|---|---|---|
| #1 (F) | AR | 7 Mar. 2014 | Sneeze, cough, chest tightness | 3 × 4 | 0 | 21 Nov. 2016 C<br>12 Dec. 2016 P | none<br>failed* |
| #2 (M) | AS | 13 Jun. 2014 | Wheeze, sneeze, chest tightness | 5 × 5 | 0 | 9 Dec. 2016 P<br>19 Dec. 2016 C | none<br>none |
| #3 (F) | AD, AR | 15 Aug. 2014 | Sneeze, cough, itchy eyes, chest tightness | 3 × 3 no erythema | 0 | 14 Nov. 2016 C | none |
| #4 (F) | AR, AD | 28 Feb. 2014 | Chest tightness, cough, itchy throat | 5 × 5 | 0 | 7 Nov. 2016 P<br>5 Dec. 2016 C | none<br>none |
| #5 (F) | AR | 4 Apr. 2014 | Cough, sneeze, rash | 5 × 5 | 0 | 31 Oct. 2016 P<br>11 Nov. 16 C | none<br>none |

AR = allergic rhinitis,
AS = asthma,
AD = atopic dermatitis,
OC = oral challenge,
SPT = skin prick test,
C = HA-GOS,
P = placebo
*Subject #1 failed the placebo challenge test; she experienced an itch on the back, chest and tongue and felt giddy.

Subject #1 experienced symptoms of an allergic response (itch on the back, chest and tongue; giddy feeling) during the challenge with placebo, whereas she passed the oral challenge test with HA-GOS without any complaints. It was confirmed by medical practitioners that the subject had received placebo prior to experiencing these allergy symptoms. This is a known phenomenon that sometimes occurs during placebo-controlled challenges, and is probably caused by anxiety of the subject.

The data in Table 10 show that all four subjects which underwent a double-blind placebo-controlled challenge with HA-GOS showed no allergic symptoms upon consumption of HA-GOS.

Results Basophil Activation Test

FIG. 2-6 show the results of the basophil activation test performed on all five subjects prior to undergoing the oral challenge test.

Figure 2B:
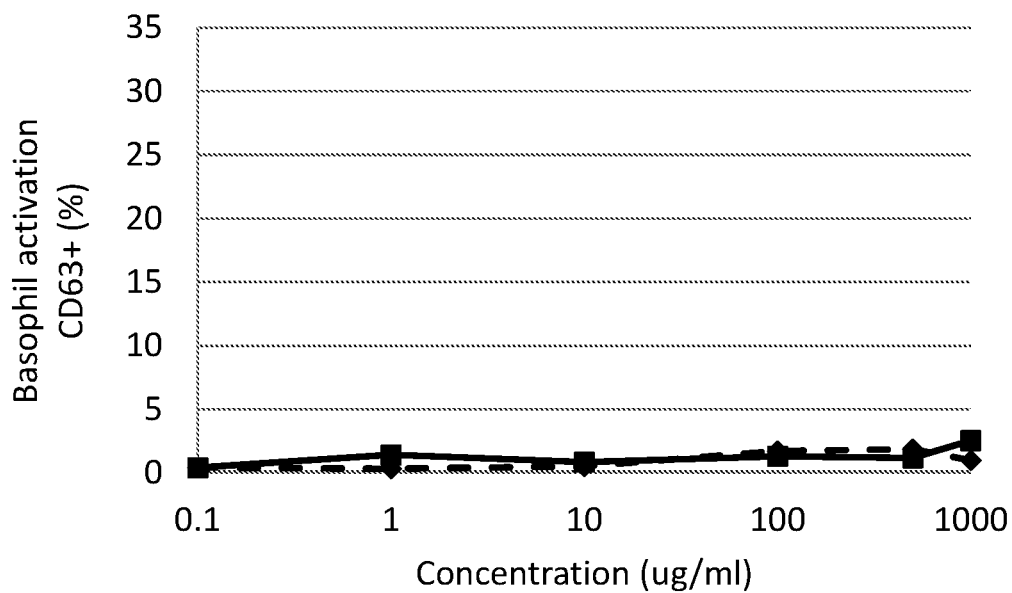
Figure 3A:
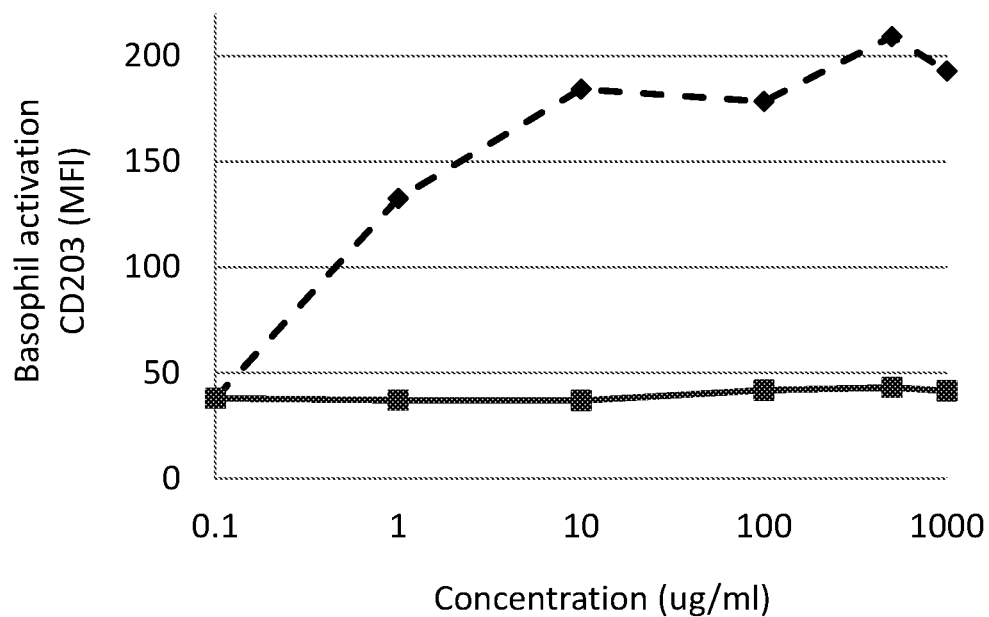
FIGS. 3a and 3b: Basophil activation in test subject #2 as measured by expression of the basophil activation marker CD203c (FIG. 3a, MFI=Mean Fluorescence) and percentage of cells expressing the basophil activation marker CD63 (FIG. 3b). Squares represent HA-GOS (solid line in the graph). Diamonds represent REF-GOS (dotted line in the graph). For details see Example 2.
Figure 3B:
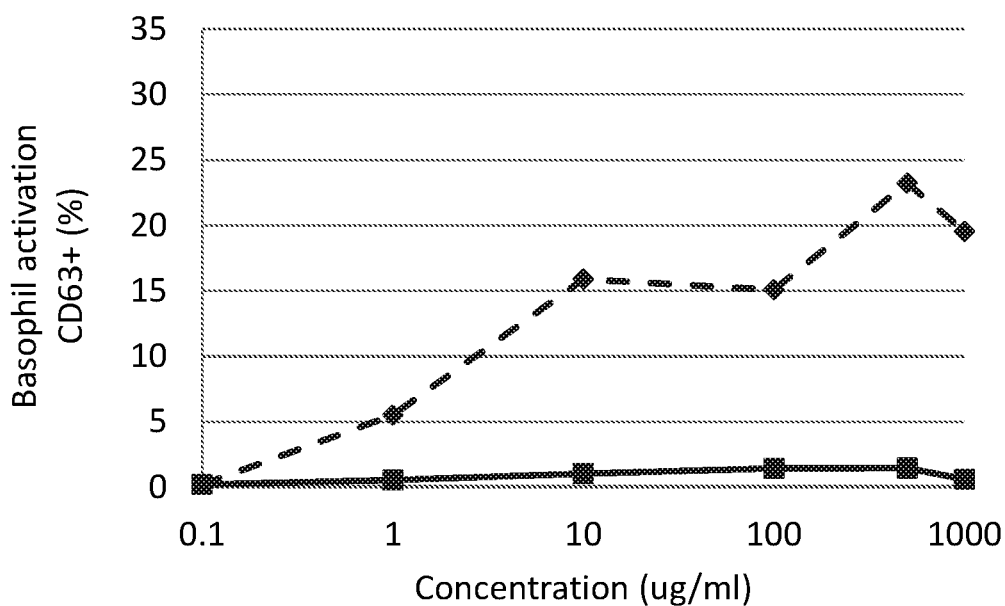
Figure 4A:
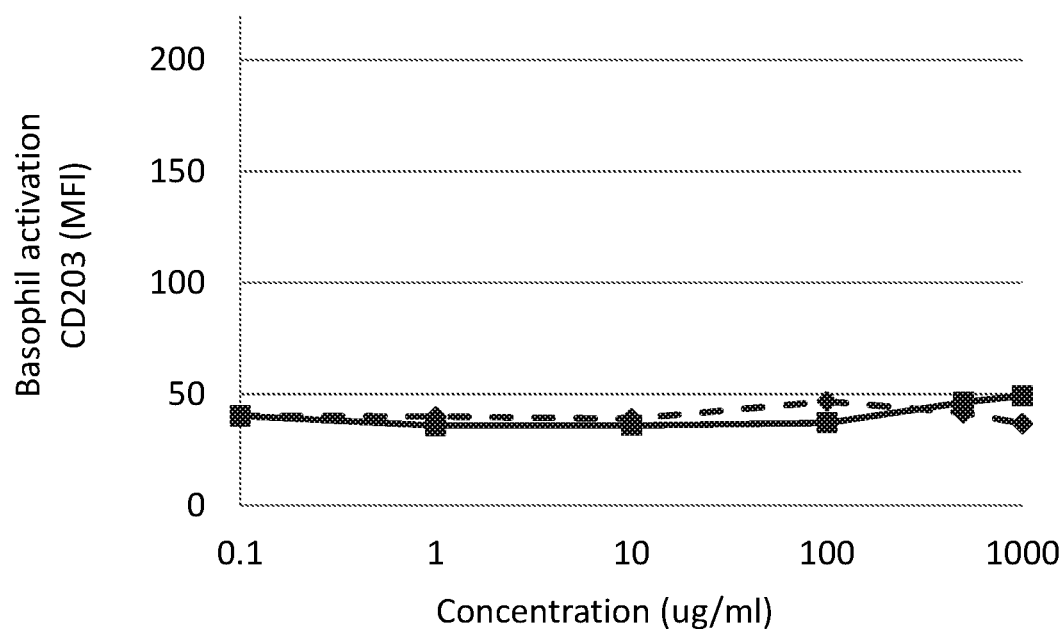
FIGS. 4a and 4b: Basophil activation in test subject #3 as measured by expression of the basophil activation marker CD203c (FIG. 4a, MFI=Mean Fluorescence) and percentage of cells expressing the basophil activation marker CD63 (FIG. 4b). Squares represent HA-GOS (solid line in the graph). Diamonds represent REF-GOS (dotted line in the graph). For details see Example 2.
Figure 4B:
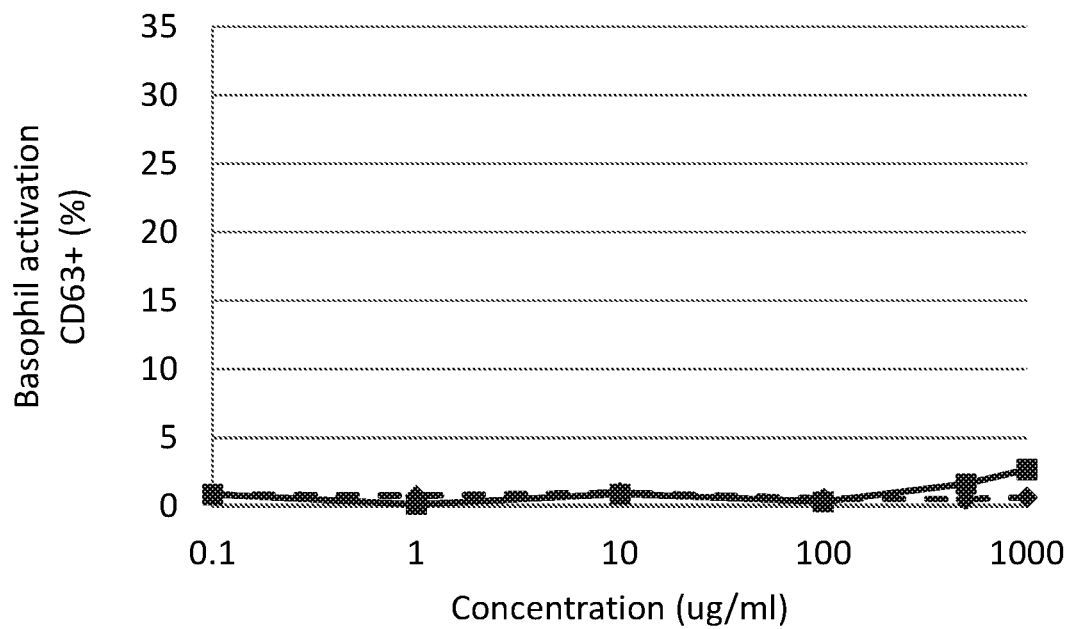
Figure 5A:
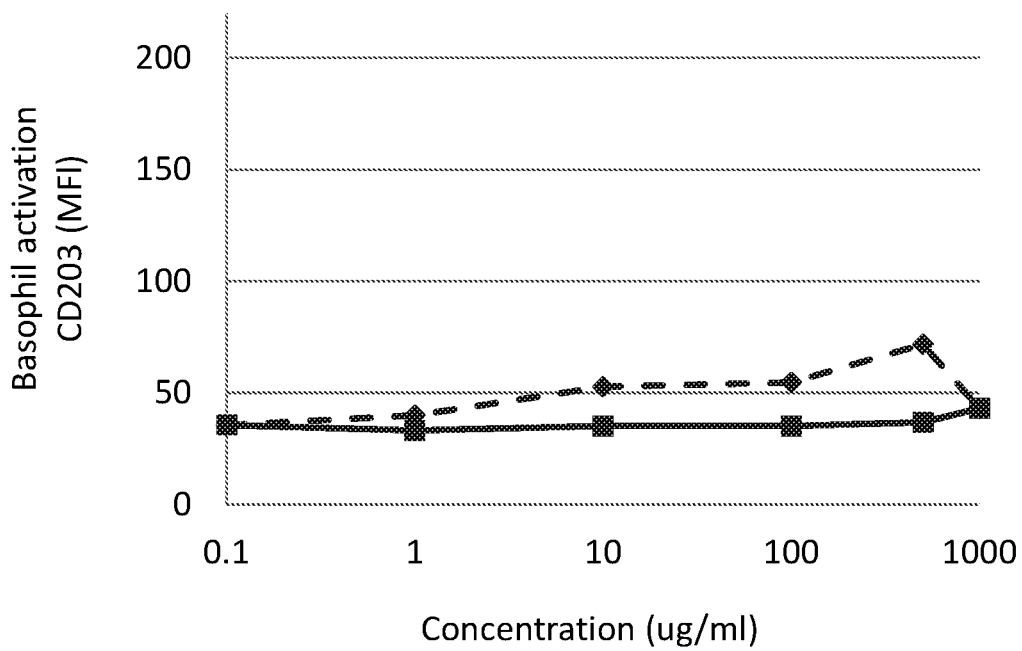
FIGS. 5a and 5b: Basophil activation in test subject #4 as measured by expression of the basophil activation marker CD203c (FIG. 5a, MFI=Mean Fluorescence) and percentage of cells expressing the basophil activation marker CD63 (FIG. 5b). Squares represent HA-GOS (solid line in the graph). Diamonds represent REF-GOS (dotted line in the graph). For details see Example 2.
Figure 5B:
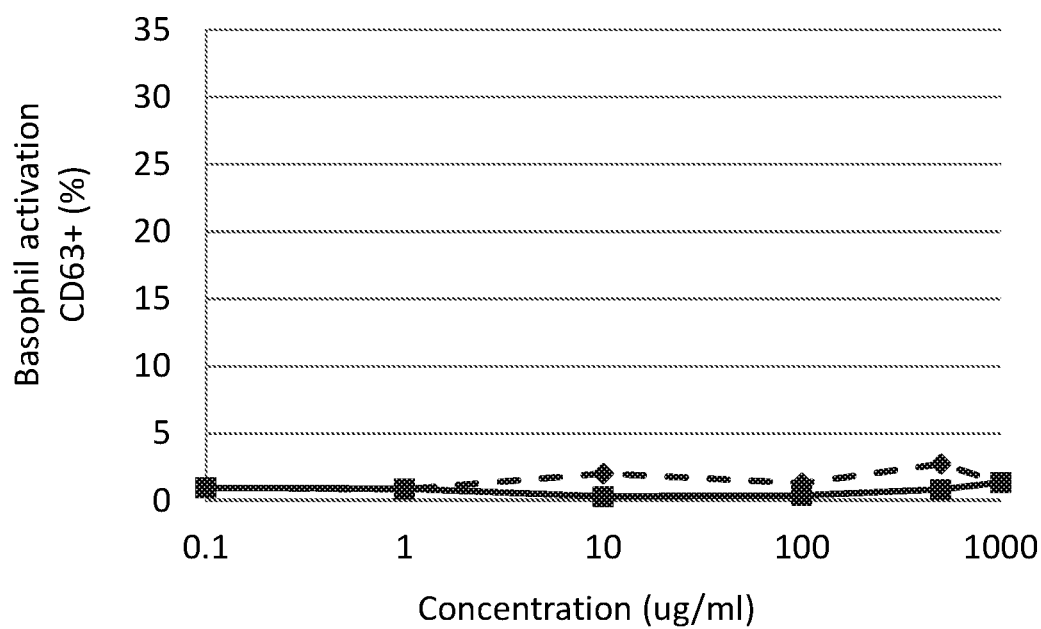
Figure 6A:
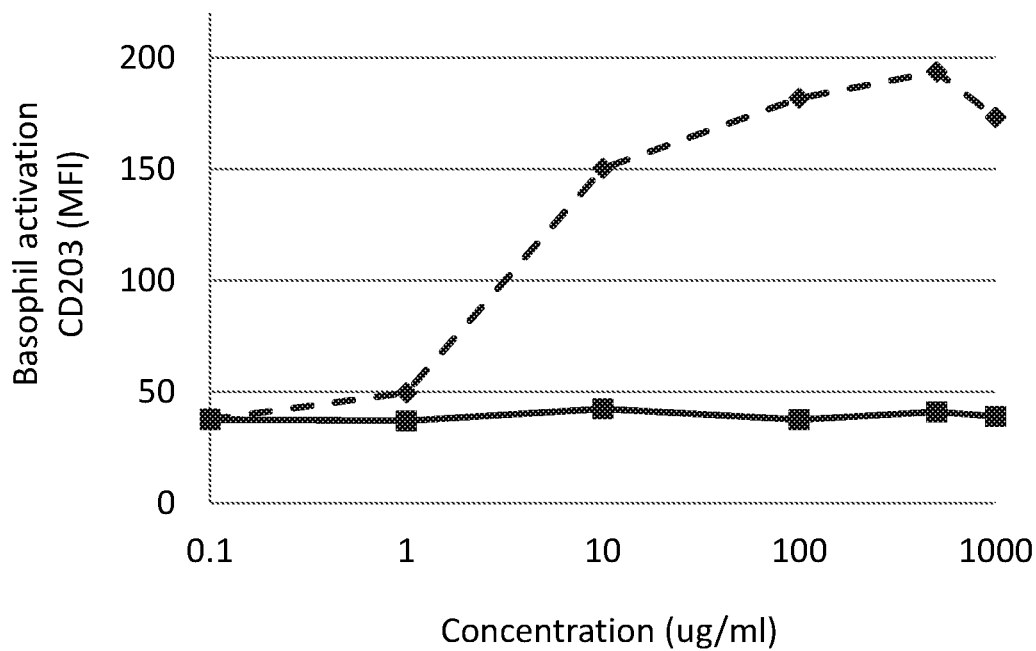
FIGS. 6a and 6b: Basophil activation in test subject #5 as measured by expression of the basophil activation marker CD203c (FIG. 6a, MFI=Mean Fluorescence) and percentage of cells expressing the basophil activation marker CD63 (FIG. 6b). Squares represent HA-GOS (solid line in the graph). Diamonds represent REF-GOS (dotted line in the graph). For details see Example 2.
Figure 6B:
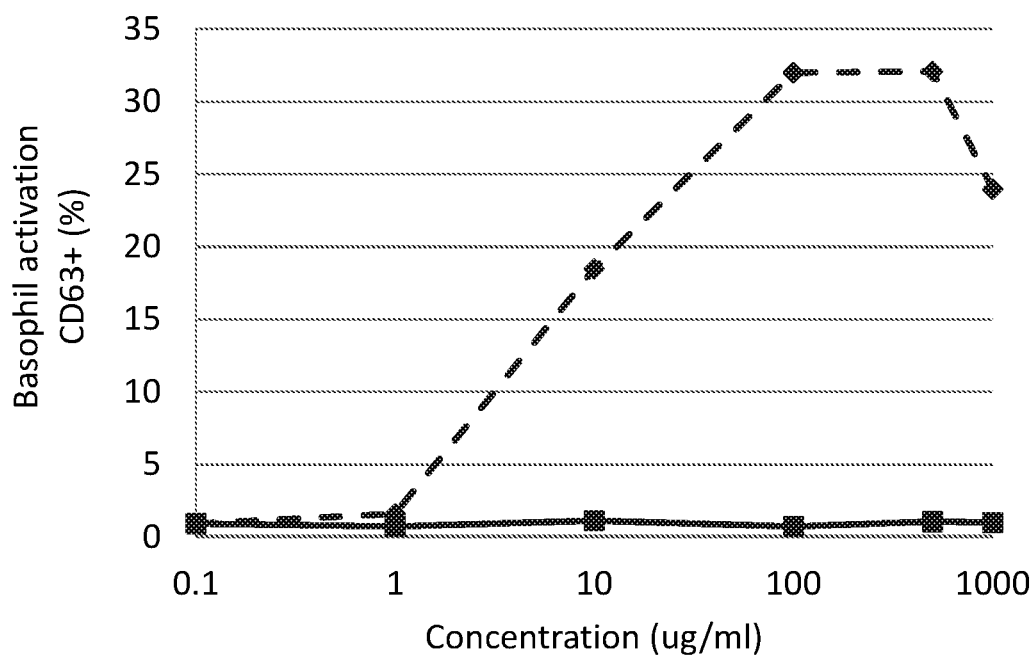

FIG. 2 shows the results of the Basophil activation in test subject #1 as measured by expression of the basophil activation marker CD203c (FIG. 2a, MFI=Mean Fluorescence) and percentage of cells expressing the basophil activation marker CD63 (FIG. 2b). Squares represent HA-GOS (solid line in the graph). Diamonds represent REF-GOS (dotted line in the graph).

Similarly, FIGS. 3, 4, 5 and 6 show the Basophil activation in test subjects #2, #3, #4 and #5, respectively, as measured by expression of the basophil activation marker CD203c (FIGS. 3a, 4a, 5a and 6a; MFI=Mean Fluorescence) and percentage of cells expressing the basophil activation marker CD63 (FIGS. 3b, 4b, 5b and 6b). Squares represent HA-GOS (solid line in the graph). Diamonds represent REF-GOS (dotted line in the graph).

The results show that three subjects (#1, #3 and #4) had a negative basophil activation response to REF-GOS. This was also previously seen during other basophil activation tests with REF-GOS. These subjects, however, are confirmed allergic to REF-GOS, since they have a positive skin prick test and oral challenge test result in response to REF-GOS. The basophil response to HA-GOS was also negative in these subjects.

Subjects #2 and #5 showed a clear basophil activation response to REF-GOS, whereas HA-GOS did not result in basophil activation.

CONCLUSIONS

HA-GOS consumption showed no allergic responses during a placebo-controlled oral challenge test in n=4 REF-GOS-allergic subjects. Skin prick tests with HA-GOS were negative in all subjects tested. Also in the basophil activation test in REF-GOS allergic subjects, clearly reduced allergenicity was found with HA-GOS as compared to REF-GOS. Taken together, it can be concluded that HA-GOS is clearly hypoallergenic in comparison to REF-GOS.

REFERENCES

1. Ben, X.-M. Low level of galacto-oligosaccharide in infant formula stimulates growth of intestinal Bifidobacteria and Lactobacilli. World J. Gastroenterol. 14, 6564 (2008).
2. Sierra, C. et al. Prebiotic effect during the first year of life in healthy infants fed formula containing GOS as the only prebiotic: a multicentre, randomised, double-blind and placebo-controlled trial. Eur. J. Nutr. 54, 89-99 (2014).
3. Fanaro, S. et al. Galacto-oligosaccharides are bifidogenic and safe at weaning: a double-blind randomized multicenter study. J. Pediatr. Gastroenterol. Nutr. 48, 82-8 (2009).
4. Sierra, C. et al. Prebiotic effect during the first year of life in healthy infants fed formula containing GOS as the only prebiotic: a multicentre, randomised, double-blind and placebo-controlled trial. Eur. J. Nutr. (2014).
5. Arslanoglu, S., Moro, G. E. & Boehm, G. Early supplementation of prebiotic oligosaccharides protects formula-fed infants against infections during the first 6 months of life. J. Nutr. 137, 2420-2424 (2007).
6. Chatchatee, P. et al. Identification of IgE and IgG binding epitopes on beta- and kappa-casein in cow's milk allergic patients. Clin. Exp. Allergy 31, 1256-62 (2001).
7. Whisner, C. M. et al. Galacto-oligosaccharides increase calcium absorption and gut bifidobacteria in young girls: a double-blind cross-over trial. Br. J. Nutr. 110, 1292-303 (2013).
8. Chiang, W. C. et al. Anaphylaxis to cow's milk formula containing short-chain galacto-oligosaccharide. J. Allergy Clin. Immunol. 130, 1361-1367 (2012).
9. Lieberman, J. A. & Sicherer, S. H. Diagnosis of food allergy: epicutaneous skin tests, in vitro tests, and oral food challenge. Curr. Allergy Asthma Rep. 11, 58-64 (2011).
10. Soh, J. Y. et al. Anaphylaxis to galacto-oligosaccharides—an evaluation in an atopic population in Singapore. Allergy 70, 1020-3 (2015).

The invention claimed is:

1. A method of at least partially preventing an allergic response to a galacto-oligosaccharide (GOS) preparation in a subject, the method comprising administering to the subject a hypoallergenic GOS preparation obtained by transgalactosylation of lactose using a *Cryptococcus terrestris* beta-galactosidase having EC 3.2.1.23, wherein the subject is known to suffer from or has hypersensitivity to a GOS preparation obtained by transgalactosylation of lactose using a *Bacillus circulans* beta-galactosidase.

2. The method according to claim 1, wherein the *Cryptococcus terrestris* beta-galactosidase is from *Cryptococcus terrestris* strain MM13-F2171 having National Institute of Technology and Evaluation (NITE) Accession Number BP-02177 or *Cryptococcus terrestris* strain APC-6431 having NITE Accession Number BP-02178.

3. The method according to claim 1, wherein the *Cryptococcus terrestris* beta-galactosidase comprises the amino acid sequence of SEQ ID NO: 1, 2, 3 or 4, or an amino acid sequence having at least 80% sequence identity to the amino acid sequence of SEQ ID NO: 1, 2, 3 or 4.

4. The method according to claim 1, wherein the hypoallergenic GOS preparation has a decreased score in a Skin Prick Test in the subject and/or in a Basophil Activation Test performed on a blood sample isolated from the subject when compared to a GOS preparation obtained by transgalactosylation of lactose using a *Bacillus circulans* beta-galactosidase.

5. The method according to claim 1, wherein the subject is of South East Asian origin.

6. The method according to claim 1, wherein the subject is an adult, an adolescent, or a child.

* * * * *